(12) United States Patent
Takagi

(10) Patent No.: US 12,233,551 B2
(45) Date of Patent: Feb. 25, 2025

(54) SYSTEM AND METHOD FOR CONTROLLING CONTINUUM ROBOT, AND CONTINUUM ROBOT

(71) Applicant: CANON KABUSHIKI KAISHA, Tokyo (JP)

(72) Inventor: Kiyoshi Takagi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 162 days.

(21) Appl. No.: 17/890,104

(22) Filed: Aug. 17, 2022

(65) Prior Publication Data

US 2022/0402130 A1 Dec. 22, 2022

Related U.S. Application Data

(63) Continuation of application No. PCT/JP2021/006085, filed on Feb. 18, 2021.

(30) Foreign Application Priority Data

Feb. 21, 2020 (JP) ................. 2020-028813

(51) Int. Cl.
*B25J 9/16* (2006.01)
*A61B 1/005* (2006.01)
(Continued)

(52) U.S. Cl.
CPC ............. *B25J 9/1633* (2013.01); *A61B 1/005* (2013.01); *B25J 9/104* (2013.01); *B25J 17/025* (2013.01)

(58) Field of Classification Search
CPC ........ B25J 9/1633; B25J 9/104; B25J 17/025; B25J 9/06; B25J 9/1625; A61B 1/005; G05B 2219/40234
See application file for complete search history.

(56) References Cited

U.S. PATENT DOCUMENTS

| | | | |
|---|---|---|---|
| 2013/0190726 A1* | 7/2013 | Kesner | A61M 25/0116 604/95.01 |
| 2014/0276933 A1* | 9/2014 | Hart | A61M 25/0147 606/130 |

(Continued)

FOREIGN PATENT DOCUMENTS

| | | |
|---|---|---|
| CN | 103200896 A | 7/2013 |
| CN | 110769984 A | 2/2020 |

(Continued)

OTHER PUBLICATIONS

Qingcong Wu, et al., "Development and hybrid force/position control of a compliant rescue manipulator", Mechatronics, Pergamon Press, vol. 46, Aug. 2017, pp. 143-153.

(Continued)

*Primary Examiner* — Abby Y Lin
*Assistant Examiner* — Dylan M Katz
(74) *Attorney, Agent, or Firm* — CANON U.S.A., INC. IP DIVISION

(57) ABSTRACT

A control system for a continuum robot including at least one curvable unit driven by a wire and configured to be curvable, and a driving unit driving the wire includes: a position control unit performing control so that an error between a target displacement of push-pull driving of the wire by the driving unit and a displacement of a wire holding mechanism holding the wire obtained from a continuum robot is compensated; a force control unit performing control so that an error between a target generated force corresponding to a target tension of the wire output from the position control unit and a generated force corresponding to a tension of the wire obtained from the continuum robot is compensated; and wherein a first loop control system including the force control unit and a second loop control system including the position control unit.

13 Claims, 27 Drawing Sheets

(51) Int. Cl.
    *B25J 9/10*     (2006.01)
    *B25J 17/02*     (2006.01)

(56) References Cited

U.S. PATENT DOCUMENTS

| | | | |
|---|---|---|---|
| 2014/0330432 A1* | 11/2014 | Simaan | B25J 9/1625 |
| | | | 700/250 |
| 2016/0213224 A1 | 7/2016 | Hatakeyama et al. | |
| 2017/0049298 A1* | 2/2017 | Hunter | A61B 5/067 |
| 2017/0312920 A1* | 11/2017 | Yip | B25J 18/06 |

FOREIGN PATENT DOCUMENTS

| | | |
|---|---|---|
| JP | H02310609 A | 12/1990 |
| JP | H0631662 A | 2/1994 |
| JP | H0720943 A | 1/1995 |
| JP | 2895352 B2 | 5/1999 |
| JP | 2011-031354 A | 2/2011 |
| JP | 2016-002414 A | 1/2016 |
| JP | 6169049 B2 | 7/2017 |
| JP | 2018-523508 A | 8/2018 |
| JP | 2019-058648 A | 4/2019 |
| JP | 2019-202137 A | 11/2019 |
| WO | 2013158978 A1 | 10/2013 |

OTHER PUBLICATIONS

Valentin Falkenhahn, et al., "Model-based feedforward position control of constant curvature continuum robots using feedback linearization", 2015 IEEE International Conference on Robotics and Automation (ICRA), IEEE, May 2015, pp. 762-767.

International Search Report and Written Opinion for PCT/JP2021/006085, including Form PCT/ISA/210 in English and including Machine Translation for Written Opinion obtained from PatentScope via WIPO IP Portal on Aug. 10, 2022.

* cited by examiner

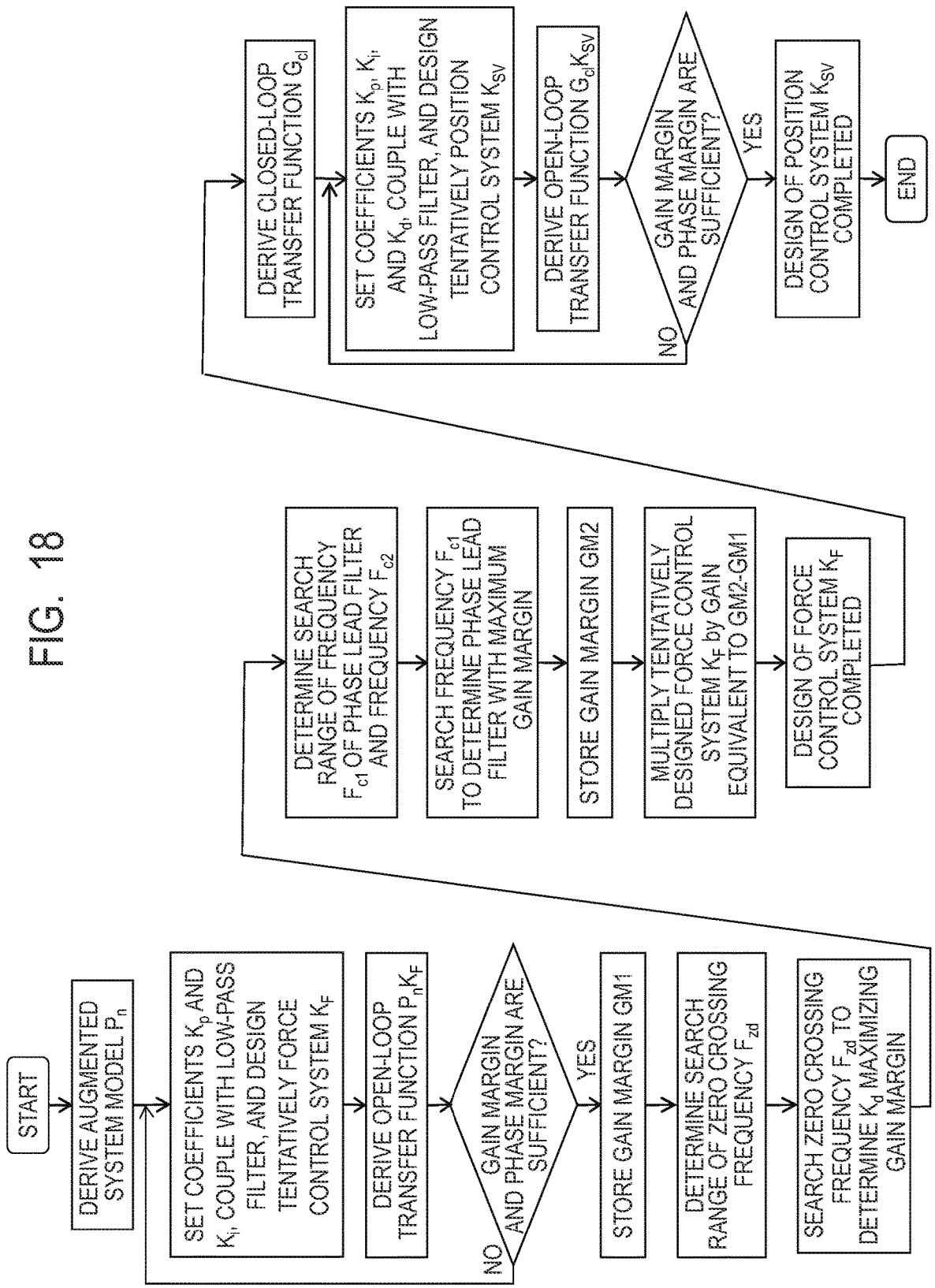

SYSTEM AND METHOD FOR CONTROLLING CONTINUUM ROBOT, AND CONTINUUM ROBOT

CROSS-REFERENCE TO RELATED APPLICATIONS

This application is a Continuation of International Patent Application No. PCT/JP2021/006085, filed Feb. 18, 2021, which claims the benefit of Japanese Patent Application No. 2020-028813, filed Feb. 21, 2020, both of which are hereby incorporated by reference herein in their entirety.

BACKGROUND OF THE DISCLOSURE

Field of the Disclosure

The present disclosure relates to a control system and a control method for a continuum robot, and the continuum robot.

Description of the Related Art

A continuum robot, also called a continuum robot, has a curvable unit having a flexible structure, and the shape of the curvable unit is controlled by deforming the curvable unit. This continuum robot has two main advantages over a robot (hereinafter referred to as "rigid link robot") composed of rigid links. The first advantage is that the continuum robot can move along the curve of an object only by manipulating the tip of the continuum robot in a narrow space or in an environment with scattered objects where a rigid link robot fits in. The second advantage is that the continuum robot has inherent softness that allows them to operate without damaging fragile objects, especially in open space. In this case, the external force detection at the end effector which is required in the rigid link robot is not necessarily required.

Taking advantage of this feature, the continuum robots are expected to be applied to medical fields such as endoscope sheaths and catheters, and extreme work robots such as rescue robots. The continuum robot may be driven by a tendon driving, a push-pull wire, an air actuator or the like.

Japanese Patent No. 6169049 discloses a control method of a manipulator which detects a load amount generated in a driving wire and controls the driving unit so that the load amount is within a predetermined range. As a result, Japanese Patent No. 6169049 allows the manipulator to be inserted into the narrow space without performing a curving operation to follow the path, thereby facilitating the insertion operation. Here, it is referred to as "back drivability" that the driving unit passively operates in accordance with the load amount. In Japanese Patent No. 6169049, detection and control algorithm of a load amount generated in a wire is used instead of a mechanism such as a clutch to prevent an increase in the size of a driving unit. Specifically, the manipulator described in Japanese Patent No. 6169049 is composed of a continuum body called a cylindrical unit and a plurality of joint structures at the tips thereof, and is operated by pulling a wire connected to the joint by a motor provided in a base end housing, and is applicable to a continuum body connected to a plurality of nodal rings by a rotating joint.

However, in the manipulator described in Japanese Patent No. 6169049, it is necessary to switch between the "insertion operation mode" in which the insertion operation is performed and the "operation control mode" in which the operator operates a tip curving unit by using the curving operation button, and the driving unit has back drivability only in the "insertion operation mode". In the manipulator described in Japanese Patent No. 6169049, the curving operation button is invalidated in the "insertion operation mode", and the tip curving unit cannot be operated. As a result, in the manipulator described in Japanese Patent No. 6169049, when selecting a narrow path having a branch or when repeating a gentle path and a steep path, the switching operation described above becomes complicated, and when the back drivability is low and the positioning performance of the curvable unit to the target position is low in a large-curvature operation, for example, a fragile object or the manipulator itself is damaged by an erroneous operation.

SUMMARY OF THE DISCLOSURE

It is an object of the present disclosure to provide a mechanism for achieving a high positioning performance of a curvable unit to a target position without requiring an operator to perform a complicated operation.

A control system of a continuum robot is a control system of the continuum robot including at least a curvable unit driven by a wire and configured to be curvable, and a driving unit driving the wire, a position control unit configured to output a target tension of the wire, wherein the position control unit performs control so that an error between a target displacement for a push-pull driving of the wire by the driving unit and a displacement of a wire holding mechanism holding the wire obtained from the continuum robot is compensated; and a force control unit configured to perform control so that an error between the target tension of the wire output from the position control unit and a tension of the wire obtained from the continuum robot is compensated, and wherein a first loop control system including the force control unit and a second loop control unit the force control unit and the position control unit are constituted. The present disclosure also includes the above-described continuum robot and a control method of the continuum robot by the control system of the continuum robot.

Further features of the present disclosure will become apparent from the following description of exemplary embodiments with reference to the attached drawings.

BRIEF DESCRIPTION OF THE DRAWINGS

FIG. 18 is a flowchart showing a design procedure of a control system according to a control apparatus of the continuum robot according to the third embodiment of the present disclosure.

DESCRIPTION OF THE EMBODIMENTS

Hereinafter, an embodiment of the present disclosure will be described with reference to the drawings.

First Embodiment

First, a first embodiment of the present disclosure will be described.

Figure 1:
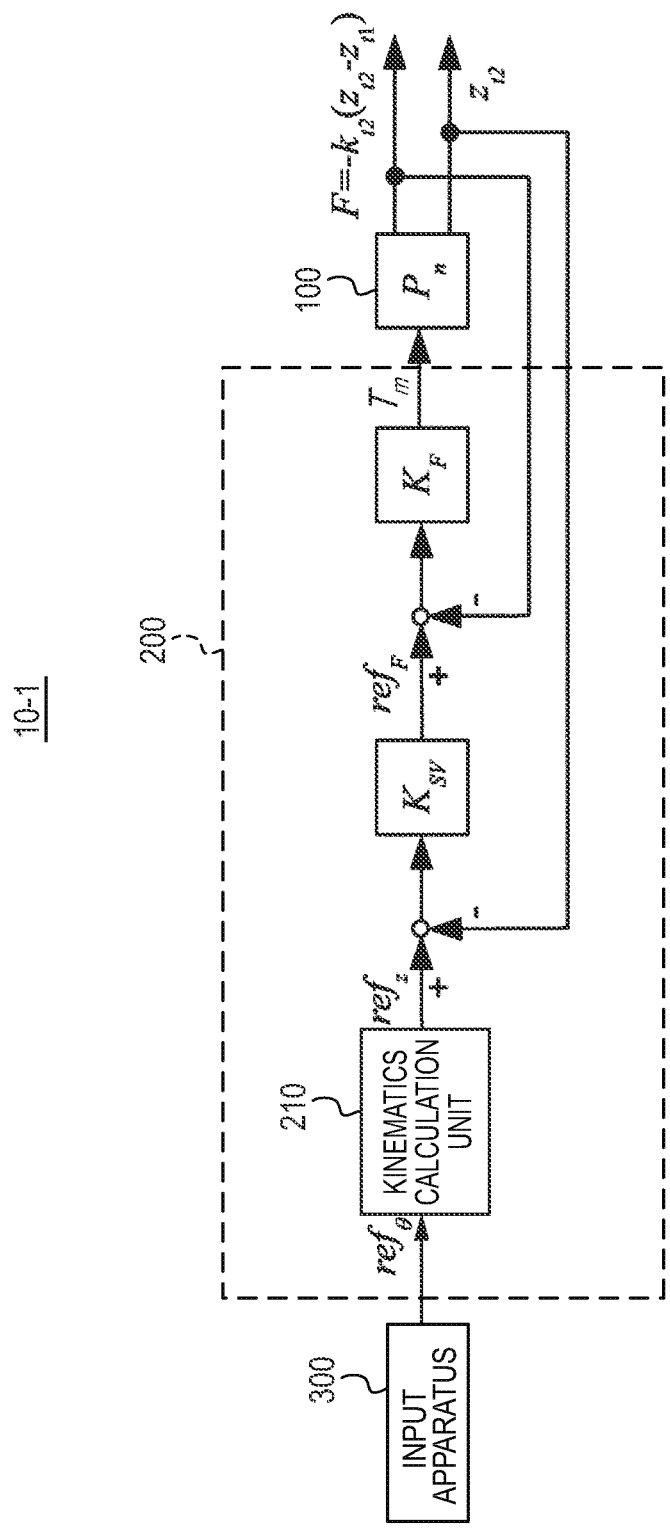
FIG. 1 is a diagram showing an example of a schematic configuration of a control system of the continuum robot according to a first embodiment of the present disclosure.

FIG. 1 is a diagram showing an example of a schematic configuration of a control system 10 of a continuum robot according to the first embodiment of the present disclosure.

Hereinafter, the control system 10 of the continuum robot shown in FIG. 1 will be described as "a control system 10-1 of the continuum robot".

As shown in FIG. 1, the control system 10-1 of the continuum robot includes a mechanism section (hereinafter referred to simply as "continuum robot") 100 of the continuum robot, a control apparatus 200 of the continuum robot, and an input apparatus 300. As shown in FIG. 1, the control apparatus 200 of the continuum robot includes a kinematics calculation unit 210, a position control unit $K_{SV}$, and a force control unit $K_F$.

In the present embodiment, the force control for the continuum robot 100 is performed by an inner loop control system (a first loop control system) including the force control unit $K_F$ shown in FIG. 1. The position of the continuum robot 100 is controlled by an outer loop control system (a second loop control system) including the force control unit $K_F$ and the position control unit $K_{SV}$ shown in FIG. 1. In the control system 10-1 of the continuum robot according to the present embodiment, a double-loop control system comprising the inner loop control system (the first loop control system) and the outer loop control system (the second loop control system) achieves high back drivability with respect to the continuum robot 100, and at the same time, high positioning performance to the target position of the curvable unit of the continuum robot 100.

In the first embodiment, a dynamic model $P_n$ of the continuum robot 100 is derived, which is driven by a wire and includes a curvable unit configured to be curvable and a driving unit driving the wire. At this time, the driving unit can detect the tension of the wire, and can be configured to include, for example, a rotary motor and a rotational linear motion conversion mechanism.

When the target curving angle refθ of the curvable unit of the continuum robot 100 (a curvable unit 110 of FIG. 2 described later) is input from the input apparatus 300, the kinematics calculation unit 210 performs kinematics calculation and outputs the target displacement $ref_z$ of the push-pull drive of the wire by the driving unit of the continuum robot 100. The position control unit $K_{SV}$ performs control for compensating an error between the target displacement $ref_z$ output from the kinematics calculation unit 210 and the displacement $z_{t2}$ of a wire holding mechanism for holding a wire obtained from a displacement sensor of the continuum robot 100, and outputs a target generated force $ref_F$ corresponding to the target tension of the wire. Here, the target generated force $ref_F$ represents a target value of the generated force F which is a positive/negative inversion value of the wire tension sensor defined in the present embodiment. The force control unit Kr performs control for compensating an error between the target generated force $ref_F$ output from the position control unit $K_{SV}$ and the generated force F corresponding to the tension of the wire obtained from the continuum robot 100, and outputs motor torque $T_m$ which is the target torque of the driving unit. A control input is given to the rotary motor or the like of the continuum robot 100.

As described above, in the inner loop control system (the first loop control system) including the force control unit $K_F$, the error is calculated by taking the difference between the target generated force $ref_F$ and the generated force F obtained from the wire tension sensor of the continuum robot 100, and the force control unit $K_F$ outputs the motor torque $T_m$ as a control input for compensating the error. This feedback loop control system is equivalent to compensating for the equivalent inertia of the rotational linear motion conversion mechanism, thereby enabling the back drivability of the continuum robot 100 to be improved. In the present embodiment, a closed-loop control system based on feedback from the inner loop control system (the first loop control system) is referred to as $G_{cl}$. In the outer loop control system (the second loop control system) including the closed-loop control system $G_{cl}$ and the position control unit $K_{SV}$, the error is calculated by taking the difference between the target displacement $ref_z$ and the displacement $z_{t2}$ obtained from the displacement sensor of the continuum robot 100, and the position control unit $K_{SV}$ outputs the target generated force $ref_F$ as a control input for compensating the error. In designing the force control unit $K_F$ and the position control unit $K_{SV}$, the stability of the feedback system is guaranteed by using a transfer function obtained from the dynamic model $P_n$ of the continuum robot 100. As a result, it is possible to realize high positioning performance to the target position while having high back drivability against disturbance of the curvable unit in the continuum robot 100.

Hereinafter, the derivation of the dynamic model $P_n$ of the continuum robot 100 and the control algorithm will be described in detail.

1.1) Modeling

Figure 2:
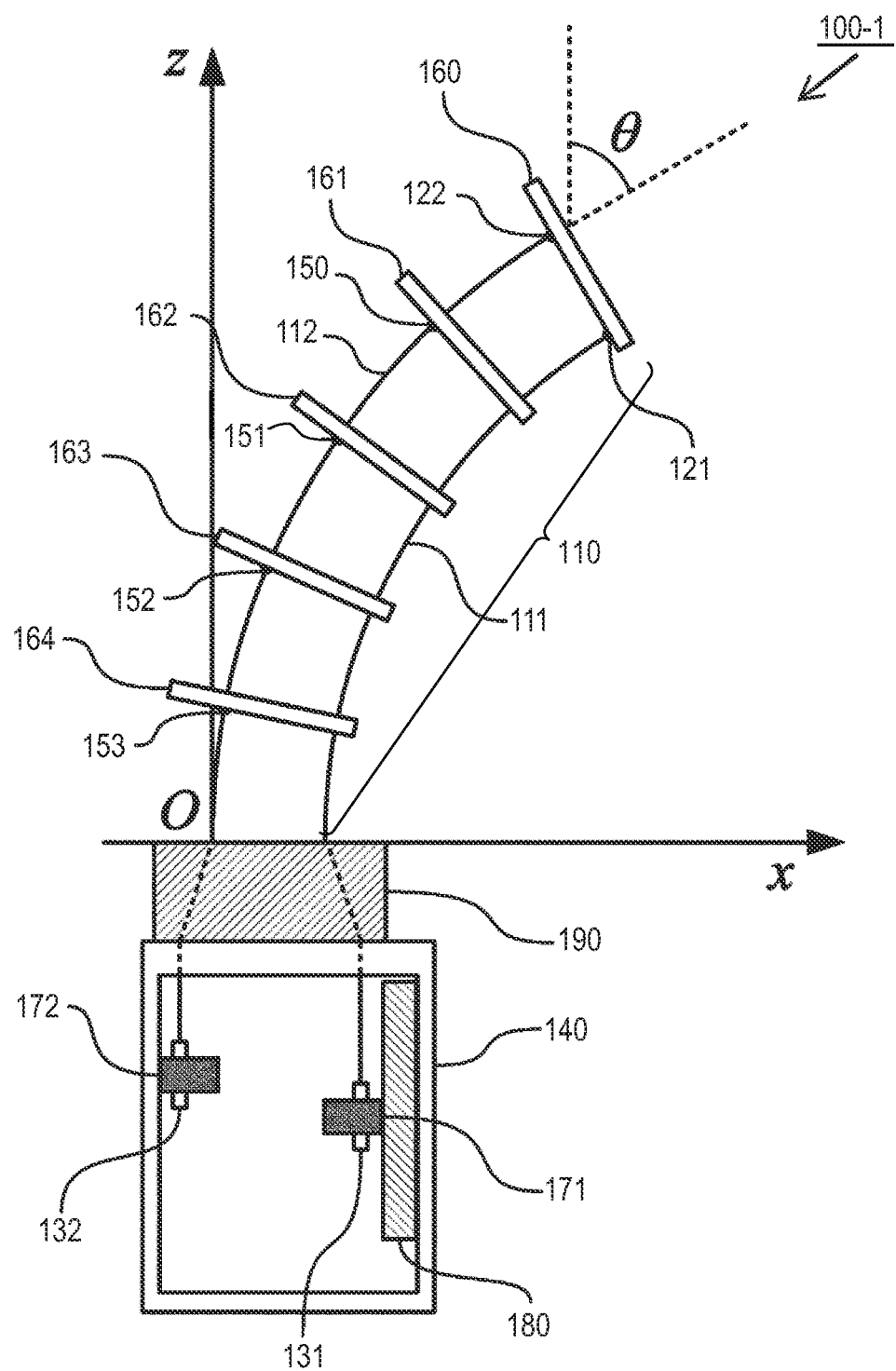
FIG. 2 shows an example of a schematic configuration of the continuum robot according to the first embodiment of the present disclosure.

FIG. 2 is a diagram showing an example of a schematic configuration of the continuum robot 100 according to the first embodiment of the present disclosure. Hereinafter, the continuum robot 100 shown in FIG. 2 will be described as "a continuum robot 100-1".

In the continuum robot 100-1, a wire 111 and a wire 112 are connected to a fixing unit 121 and a fixing unit 122 at a distal end 160 of the curvable unit 110, respectively. The proximal ends of the wire 111 and the wire 112 are connected to a wire holding pipe 131 and a wire holding pipe 132, respectively, in a robot base unit 140. A wire holding mechanism 171 for supporting the wire holding pipe 131, a wire holding mechanism 172 for supporting the wire holding pipe 132, and an actuator 180 corresponding to a driving unit are arranged on the robot base unit 140. At this time, the wire holding mechanism 172 is fixed to the robot base unit 140. The wire holding mechanism 171 is connected to the actuator 180 as a driving unit through a wire holding mechanism base unit (not shown), and is movable up and down. The wire holding pipe 131 is connected to the wire holding mechanism 171 so as to be supported, and the attitude of the curvable unit 110 is controlled by pressing and pulling by the actuator 180. The continuum robot 100-1 has the wire 111 and wire guides 161-164 serving as a member for guiding the wire 112. The wire guide may be a continuum member such as a bellows member or a mesh member in addition to a method of discretely arranging a plurality of members. The wire guides 161-164 are fixed to the wire 112 at fixing units 150-153. Further, the distance between the wire 111 and the wire 112 may be different from the distance between the wire holding mechanism 171 and the wire holding mechanism 172. In this case, a diameter conversion unit 190 is connected to the robot base unit 140.

In the present embodiment, the mechanism comprising the wires 111 and 112, and the wire guides 161-164 are referred to as the curvable unit 110, which is a continuum portion. As the actuator 180, an actuator unit comprising a rotary motor and a rotational linear motion conversion mechanism is used. Further, the wire holding mechanism 171 (or the actuator 180) has a function of detecting the tension of the wire 111. For this purpose, the above-described wire holding mechanism base unit (not shown) is provided between the wire holding mechanism 171 and the actuator 180, the wire holding mechanism base is connected to the actuator 180, and the wire holding mechanism base unit and the wire holding mechanism 171 are connected by a spring. At this time, it is preferable to provide a linear guide so that the wire holding mechanism 171 is displaced only in the z-axis direction, or to use a parallel spring for the spring. The tension of the wire 111 can be detected by measuring the displacement of the spring.

Figure 3C:
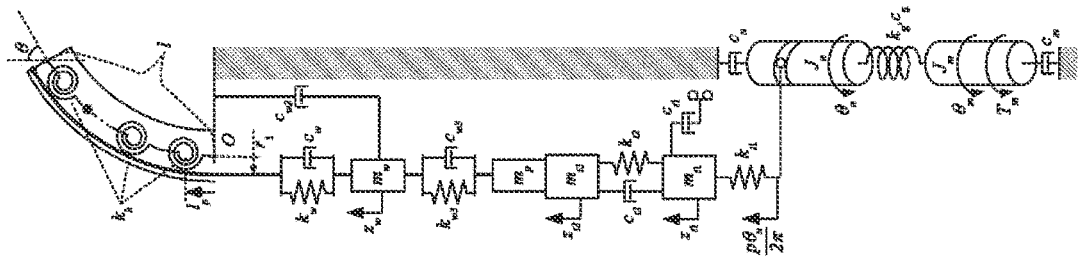
FIG. 3C shows an example of coupling of a dynamic model comprising a rotary motor, a rotational linear motion conversion mechanism, a wire holding mechanism, and the like with a dynamic model of the continuum robot according to the first embodiment of the present disclosure.
Figure 3B:
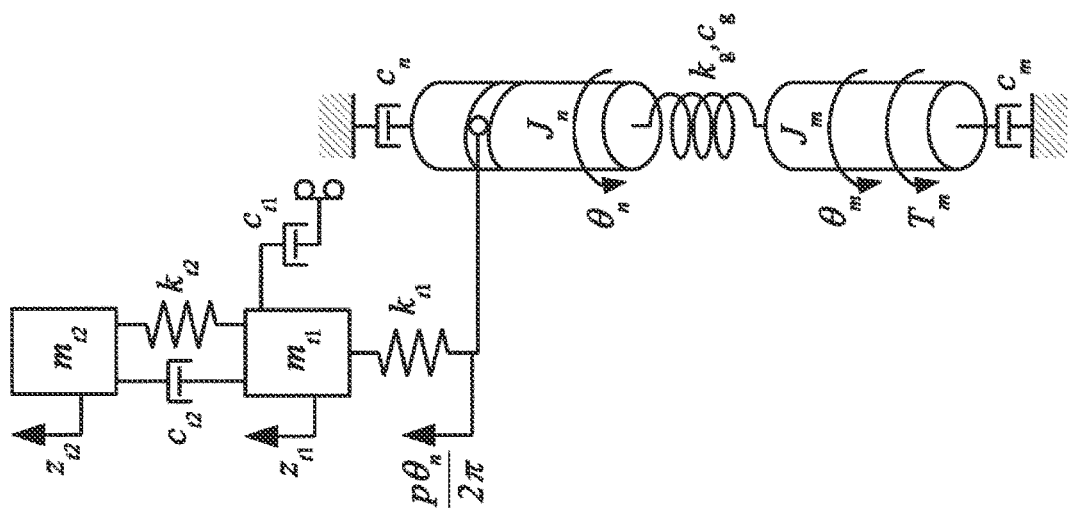
FIG. 3B shows an example of a dynamic model including a rotary motor, a rotational linear motion conversion mechanism, a wire holding mechanism and the like included in an actuator according to the first embodiment of the present disclosure.
Figure 3A:
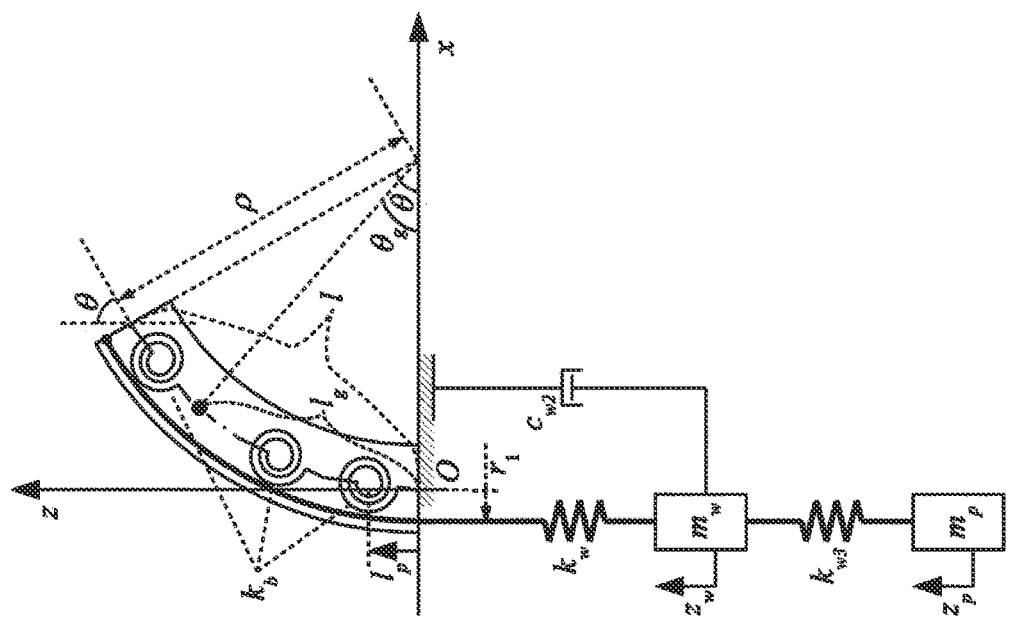
FIG. 3A shows an example of a dynamic model of the continuum robot according to the first embodiment of the present disclosure.

FIGS. 3A to 3C show an example of a dynamic model $P_n$ of the continuum robot 100 according to the first embodiment of the present disclosure. Specifically, FIG. 3A shows an example of the dynamic model of the curvable unit 110, which is a continuum portion, and FIG. 3B shows an example of a dynamic model including the rotary motor included in the actuator 180, the rotational linear motion conversion mechanism, the wire holding mechanism 171, and the like.

1.1.1) Dynamic Model of the Curvable Unit 110, which is a Continuum Portion

The definition of the sign in the dynamic model of the curvable unit 110, which is the continuum portion shown in FIG. 3A, is described below.

θ: Curving angle of the curvable unit 110 of the continuum robot.

ρ: Radius of curvature.

l: Length of the curvable unit 110.

n: Distance from the central axis of the curvable unit 110 to the wire.

$l_p$: Amount of the wire driven.

$m_s$: Mass of the curvable unit 110.

$k_b$: Spring coefficient for the curving angle of the curvable unit 110.

$z_w$: Displacement of the wire equivalent mass.

$z_p$: Displacement of the wire holding pipe.

$m_w$: Mass of the wire.

$m_p$: Mass of the wire holding pipe.

$k_w$, $k_{w3}$: Spring coefficient of the wire.

$c_w$, $c_{w3}$: Damping coefficient of the wire.

$c_{w2}$: Damping coefficient due to friction between the wire, and the diameter conversion unit and the wire guide.

Subsequently, a motion equation of the continuum robot 100-1 is derived.

In the present embodiment, the following assumptions are made.

[1] Only motion in a two-dimensional plane is considered.

[2] The curvature of the curvable unit 110 is constant and the spring coefficient is uniform.

[3] The wire is approximated as a lumped mass system, and a reaction force due to deformation in the longitudinal direction acts on the tip of the curvable unit 110. Transverse vibration and lateral deformation of the wire are not considered.

[4] The friction between the wire and the wire guide and the friction between the wire and the diameter conversion unit, including nonlinear friction such as Coulomb friction, are included into the damping coefficient $c_{w2}$ as viscous damping.

First, the kinetic energy of the curvable unit 110 is obtained. When displacements $x_g$ and $z_g$ are taken on the central axis of the curvable unit 110, the following equations (1) and (2) are obtained, respectively.

$$x_g = \frac{l_g}{\theta_g}(1 - \cos\theta_g) \quad (1)$$

$$z_g = \frac{l_g}{\theta_g}\sin\theta_g \quad (2)$$

Based on the following equation (3), $$\theta_g = \frac{l_g}{l}\theta \quad (3)$$

the displacements $x_g$ and $z_g$ are the following equations (4) and (5), respectively.

$$x_g = \frac{l}{\theta}\left(1 - \cos\frac{l_g}{l}\theta\right) \quad (4)$$

$$z_g = \frac{l}{\theta}\sin\frac{l_g}{l}\theta \quad (5)$$

Using them, the kinetic energy $T_a$ of the curvable unit 110 is expressed by the following equation (6).

$$T_a = \frac{m_s}{2l}\int_0^l (\dot{x}_g^2 + \dot{z}_g^2)dl_g \quad (6)$$
$$= \frac{m_s(12l^3\sin\theta - 6l^3\theta\cos\theta - l^3\theta^3 - 6l^3\theta)\dot{\theta}^2}{6l\theta^5}$$

The potential energy $U_a$ of the curvable unit 110 is expressed by the following equation (7).

$$U_a = \frac{1}{2}k_b\theta^2 \quad (7)$$

Next, since the wire driving amount is $l_p = r_1\theta$, the kinetic energy $T_w$ and the potential energy $U_w$ of the wire and the wire holding pipe are expressed by the following expressions (8) and (9), respectively.

$$T_w = \frac{1}{2}m_w\dot{z}_w^2 + \frac{1}{2}m_p\dot{z}_p^2 \quad (8)$$

$$U_w = \frac{1}{2}k_w(r_1\theta - z_w)^2 + \frac{1}{2}k_{w3}(z_w - z_p)^2 \quad (9)$$

Then, when the motion equation is obtained from the following equation (10) showing the Lagrange equation, $$\frac{d}{dt}\left(\frac{\partial T}{\partial \dot{q}_i}\right) - \frac{\partial T}{\partial q_i} + \frac{\partial U}{\partial q_i} = Q_i \quad i = 1, 2 \quad (10)$$

$$T = T_a + T_w, \quad U = U_a + U_w$$

$$q = [q_1, q_2, q_3]^T = [z_p, z_w, \theta]^T$$

$$Q = [Q_1, Q_2, Q_3]^T = [0, 0, 0]^T$$

a nonlinear differential equation shown in the following equation (11) is obtained. In the following equation (11), the term $\Phi$ is a nonlinear term that cannot be included in $M_c$, $C_c$, and $K_c$.

$$M_c\ddot{q} + K_c q + C_c \dot{q} + \Phi = \quad (11)$$

$$\begin{bmatrix} m_p & 0 & 0 \\ 0 & m_w & 0 \\ 0 & 0 & M_{c22} \end{bmatrix}\begin{bmatrix} \ddot{z}_p \\ \ddot{z}_w \\ \ddot{\theta} \end{bmatrix} + \begin{bmatrix} k_{w3} & -k_{w3} & 0 \\ -k_{w3} & k_{w3}+k_w & -k_w r \\ 0 & -k_w r & k_w r^2 + k_b \end{bmatrix}\begin{bmatrix} z_p \\ z_w \\ \theta \end{bmatrix} +$$

$$\begin{bmatrix} c_{w3} & -c_{w3} & 0 \\ -c_{w3} & c_{w3}+c_w+c_{w2} & -c_w r \\ 0 & -c_w r & c_w r^2 + c_b \end{bmatrix}\begin{bmatrix} \dot{z}_p \\ \dot{z}_w \\ \dot{\theta} \end{bmatrix} + \begin{bmatrix} 0 \\ 0 \\ \Phi_3 \end{bmatrix} = \begin{bmatrix} 0 \\ 0 \\ 0 \end{bmatrix}$$

Further, $M_{c22}$ and $\Phi_3$ of equation (11) are the following equations (12) and (13).

$$M_{c22} = -\frac{l^2 m_s(12\sin\theta - 6\theta\cos\theta - \theta^3 - 6\theta)}{3\theta^5} \quad (12)$$

$$\Phi_3 = -\frac{\dot{\theta}^2 l^2 m_s(3\theta^2\sin\theta - 30\sin\theta + 18\theta\cos\theta + \theta^3 + 12\theta)}{3\theta^5} \quad (13)$$

However, when the curving angle of the curvable unit 110 is in the vicinity of 0 degrees, the expressions (12) and (13) become undefined and the value cannot be obtained. Therefore, a 0 degrees neighborhood linearization model without considering large deformation is obtained. From equations (4) and (5), the following equation (14) is obtained.

$$x_{g0} = \lim_{\theta \to 0} x_g = \frac{l_g^2 \theta}{2l}, \quad z_{g0} = \lim_{\theta \to 0} z_g = l_g \quad (14)$$

The kinetic energy $T_{a0}$ in the vicinity of 0 degrees of the curvable unit 110 is expressed by the following equation (15).

$$T_{a0} = \frac{m_s}{2l}\int_0^l (\dot{x}_{g0}^2 + \dot{z}_{g0}^2)dl_g = \frac{m_s}{40}l^2\dot{\theta}^2 \quad (15)$$

Then, to obtain the following equation (16), the motion equation is obtained from the Lagrange equation where $T = T_{a0} + T_w$.

$$M_{c0}\ddot{q} + K_{c0}q + C_{c0}\dot{q} = \begin{bmatrix} m_p & 0 & 0 \\ 0 & m_w & 0 \\ 0 & 0 & \frac{l^2 m_s}{20} \end{bmatrix}\begin{bmatrix} \ddot{z}_p \\ \ddot{z}_w \\ \ddot{\theta} \end{bmatrix} + \quad (16)$$

$$\begin{bmatrix} k_{w3} & -k_{w3} & 0 \\ -k_{w3} & k_{w3}+k_w & -k_w r \\ 0 & -k_w r & k_w r^2 + k_b \end{bmatrix}\begin{bmatrix} z_p \\ z_w \\ \theta \end{bmatrix} +$$

$$\begin{bmatrix} c_{w3} & -c_{w3} & 0 \\ -c_{w3} & c_{w3}+c_w+c_{w2} & -c_w r \\ 0 & -c_w r & c_w r^2 + c_b \end{bmatrix}\begin{bmatrix} \dot{z}_p \\ \dot{z}_w \\ \dot{\theta} \end{bmatrix} = \begin{bmatrix} 0 \\ 0 \\ 0 \end{bmatrix}$$

1.1.2) Dynamic Model Including Rotary Motor, Rotational Linear Motion Conversion Mechanism, and Wire Holding Mechanism FIG. 3B is a diagram showing an example of a dynamic model comprising a rotary motor, a rotational linear motion conversion mechanism, and a wire holding mechanism. The wire holding mechanism has a function of detecting the tension of the wire, a wire holding mechanism base is provided between the wire holding mechanism and the actuator 180, the wire holding mechanism base is connected to the actuator 180, and the wire holding mechanism base and the wire holding mechanism are connected by a spring. Tension is detected by detecting the displacement of the spring. The definition of the sign in the dynamic model shown in FIG. 3B is described below.

$J_m$: Inertia of the motor.
$\theta_m$: Rotation angle of the motor.
$T_m$: Target torque of the motor (command value).
$c_m$: Damping coefficient of the motor shaft.
$k_g$, $c_g$: Spring coefficient and damping coefficient of the coupling.
$J_n$: Inertia of the drive shaft.
$\theta_n$: Rotation angle of the drive shaft.
$c_n$: Damping coefficient of the drive shaft.
$p$: Thread pitch of the drive shaft.
$R$: Conversion factor of the linear rotation conversion mechanism which is equivalent speed increasing ratio.
$m_{t1}$: Mass of the wire holding mechanism base unit.
$k_{t1}$: Spring factor in z-direction of the drive shaft.
$c_{t1}$: Damping coefficient of the linear slider of the wire holding mechanism base unit.
$z_{t1}$: Displacement of the wire holding mechanism base unit.
$m_{t2}$: Mass of the wire holding mechanism.
$k_{t2}$, $c_{t2}$: Spring coefficient and damping coefficient of the tension detection mechanism.
$z_{t2}$: Displacement of the wire holding mechanism.

The motion equations are expressed by the following equations (17) to (20).

$$J_m\ddot{\theta}_m = T_m + k_g(\theta_n - \theta_m) + c_g(\dot{\theta}_n - \dot{\theta}_m) - c_m\dot{\theta}_m \quad (17)$$

$$J_n\ddot{\theta}_n = -k_g(\theta_n - \theta_m) - c_g(\dot{\theta}_n - \dot{\theta}_m) + Rk_{t1}(z_{t1} - R\theta_n) - c_n\dot{\theta}_n \quad (18)$$

$$m_{t1}\ddot{z}_{t1} = -k_{t1}(z_{t1} - R\theta_n) + k_{t2}(z_{t2} - z_{t1}) - c_{t1}\dot{z}_{t1} + c_{t2}(\dot{z}_{t2} - \dot{z}_{t1}) \quad (19)$$

$$m_{t2}\ddot{z}_{t2} = -k_{t2}(z_{t2} - z_{t1}) - c_{t2}(\dot{z}_{t2} - \dot{z}_{t1}) \quad (20)$$

Here, $R = p/2\pi$ is assumed. The matrix representation of $q_1 = [\theta_m, \theta_n, z_{t1}, z_{t2}]^T$ gives the following equation (21).

$$M_l\ddot{q}_l + K_l q_l + C_l\dot{q}_l = \begin{bmatrix} J_m & & & 0 \\ & J_n & & \\ & & m_{t1} & \\ 0 & & & m_{t2} \end{bmatrix}\begin{bmatrix} \ddot{\theta}_m \\ \ddot{\theta}_n \\ \ddot{z}_{t1} \\ \ddot{z}_{t2} \end{bmatrix} +$$

$$\begin{bmatrix} k_g & -k_g & 0 & 0 \\ -g_g & k_g + R^2 k_{t1} & -Rk_{t1} & 0 \\ 0 & -Rk_{t1} & k_{t1} + k_{t2} & -k_{t2} \\ 0 & 0 & -k_{t2} & k_{t2} \end{bmatrix}\begin{bmatrix} \theta_m \\ \theta_n \\ z_{t1} \\ z_{t2} \end{bmatrix} +$$

$$\begin{bmatrix} c_m + c_g & -c_g & 0 & 0 \\ -c_g & c_n + c_g & 0 & 0 \\ 0 & 0 & c_{t1} + c_{t2} & -c_{t2} \\ 0 & 0 & -c_{t2} & c_{t2} \end{bmatrix}\begin{bmatrix} \dot{\theta}_m \\ \dot{\theta}_n \\ \dot{z}_{t1} \\ \dot{z}_{t2} \end{bmatrix} = \begin{bmatrix} T_m \\ 0 \\ 0 \\ 0 \end{bmatrix} \quad (21)$$

1.1.3) Configuration of the Augmented System

As shown in FIG. 3C, a dynamic model of the curvable unit 110 is coupled to a dynamic model comprising a rotary motor, the rotational linear motion conversion mechanism, and the wire holding mechanism. When the augmented system is constituted by equations (11) and (21) by making the displacement of the wire holding mechanism $z_{t2}$ and the displacement of the wire holding pipe $z_p$ the same, the motion equation is expressed by following equation (22). Here, $q_g = [q_l^T, z_w, \theta]^T$.

$$M_g\ddot{q}_g + K_g q_g + C_g\dot{q}_g + \Phi_g = \begin{bmatrix} J_m & & & & & 0 \\ & J_n & & & & \\ & & m_{t1} & & & \\ & & & m_{t2} + m_p & & \\ & & & & m_w & \\ 0 & & & & & M_{c22} \end{bmatrix}\begin{bmatrix} \ddot{\theta}_m \\ \ddot{\theta}_n \\ \ddot{z}_{t1} \\ \ddot{z}_{t2} \\ \ddot{z}_w \\ \ddot{\theta} \end{bmatrix} +$$

$$\begin{bmatrix} k_g & -k_g & 0 & 0 & 0 & 0 \\ -k_g & k_g + R^2 k_{t1} & -Rk_{t1} & 0 & 0 & 0 \\ 0 & -Rk_{t1} & k_{t1} + k_{t2} & -k_{t2} & 0 & 0 \\ 0 & 0 & -k_{t2} & k_{t2} + k_{w3} & -k_{w3} & 0 \\ 0 & 0 & 0 & -k_{w3} & k_{w3} + k_w & -k_w r \\ 0 & 0 & 0 & 0 & -k_w r & k_w r^2 + k_b \end{bmatrix}\begin{bmatrix} \theta_m \\ \theta_n \\ z_{t1} \\ z_{t2} \\ z_w \\ \theta \end{bmatrix} +$$

$$\begin{bmatrix} c_m + c_g & -c_g & 0 & 0 & 0 & 0 \\ -c_g & c_n + c_g & 0 & 0 & 0 & 0 \\ 0 & 0 & c_{t1} + c_{t2} & -c_{t2} & 0 & 0 \\ 0 & 0 & -c_{t2} & c_{t2} + c_{w3} & -c_{w3} & 0 \\ 0 & 0 & 0 & -c_{w3} & c_{w3} + c_w + c_{w2} & -c_w r \\ 0 & 0 & 0 & 0 & -c_w r & c_w r^2 + c_b \end{bmatrix}\begin{bmatrix} \dot{\theta}_m \\ \dot{\theta}_n \\ \dot{z}_{t1} \\ \dot{z}_{t2} \\ \dot{z}_w \\ \dot{\theta} \end{bmatrix} +$$

$$\begin{bmatrix} 0 \\ 0 \\ 0 \\ 0 \\ 0 \\ \Phi_3 \end{bmatrix} = \begin{bmatrix} 1 \\ 0 \\ 0 \\ 0 \\ 0 \\ 0 \end{bmatrix} T_m \quad (22)$$

Next, the state equation is obtained. When the curving angle of the curvable unit 110 is not in the vicinity of 0 degrees, the following extended linearization method of equation (23) is applied in which the nonlinear term $\Phi_g$ is included into the matrix $K_g$ to perform linearization.

$$\Phi_3 = \frac{\Phi_3}{\theta}\theta \quad (23)$$

Thereby, $\Phi_3$ becomes an element of $K_g(6, 6)$. The state equation is expressed by the following equations (24) and (25).

$$\dot{x}_g = A_g(\theta,\dot\theta)x_g + B_g(\theta,\dot\theta)T_m \quad (24)$$

$$x_g = [\theta_m, \theta_n, z_{t1}, z_{t2}, z_w, \theta, \dot\theta_m, \dot\theta_n, \dot z_{t1}, \dot z_{t2}, \dot z_w, \dot\theta]^T \quad (25)$$

In the present embodiment, the displacement $z_{t1}$ of the wire holding mechanism base unit and the displacement $z_{t2}$ of the wire holding mechanism can be measured, and the force (hereinafter referred to as generating force) F generated by the spring displacement $k_{t2}$ exerts on the wire holding mechanism and the displacement $z_{t2}$ of the wire holding mechanism are taken as observation quantities. Here, the generated force F is expressed by the following equation (26).

$$F = -k_{t2}(z_{t2} - z_{t1}) \quad (26)$$

In this case, the observed quantity $y_g$ is expressed by the output equation shown in the following equation (27).

$$\begin{aligned} y_g &= [-k_{t2}(z_{t2} - z_{t1}) z_{t2}]^T \quad (27)\\ &= \begin{bmatrix} 0 & 0 & k_{t2} & -k_{t2} & 0 & 0 & 0 & 0 & 0 & 0 & 0 & 0 \\ 0 & 0 & 0 & 1 & 0 & 0 & 0 & 0 & 0 & 0 & 0 & 0 \end{bmatrix} x_g \\ &= C_g x_g \end{aligned}$$

When the curving angle of the curvable unit 110 is in the vicinity of 0 degrees, an augmented system is similarly constituted by equation (16) showing the motion equation of the curvable unit 110 in the vicinity of 0 degrees and equation (21) showing the motion equation of a dynamic model consisting of the rotary motor and a rotational linear motion conversion mechanism, and a wire holding mechanism. Since this is a linear model, it can be directly converted into a state equation.

1.2) Model Analysis 1.2.1) Variation Relative to the Equivalent Speed Increasing Ratio R In the present chapter, a model analysis is performed to examine the variation of poles and zeros of the curvable unit 110 according to the equivalent speed increasing ratio R of the rotational linear motion conversion mechanism. In the present embodiment, the variation of the phase due to a damping coefficient $c_{w2}$ between the wire, and the diameter conversion unit and the wire guide will be described. Here, it is assumed that the lowest natural frequency of the curvable unit 110 is 62 Hz. At this time, the equivalent inertia of the rotational linear motion conversion mechanism is changed by changing the equivalent speed increasing ratio R of the rotational linear motion conversion mechanism from 1 to 10,000 times of the design parameter, and the variation of the poles and the zeros is examined. In addition, in this analysis, in order to make the variation between the poles and the zeros easy to understand, the damping coefficients of each part of the curvable unit 110 are set to be substantially 0.

Figure 4:
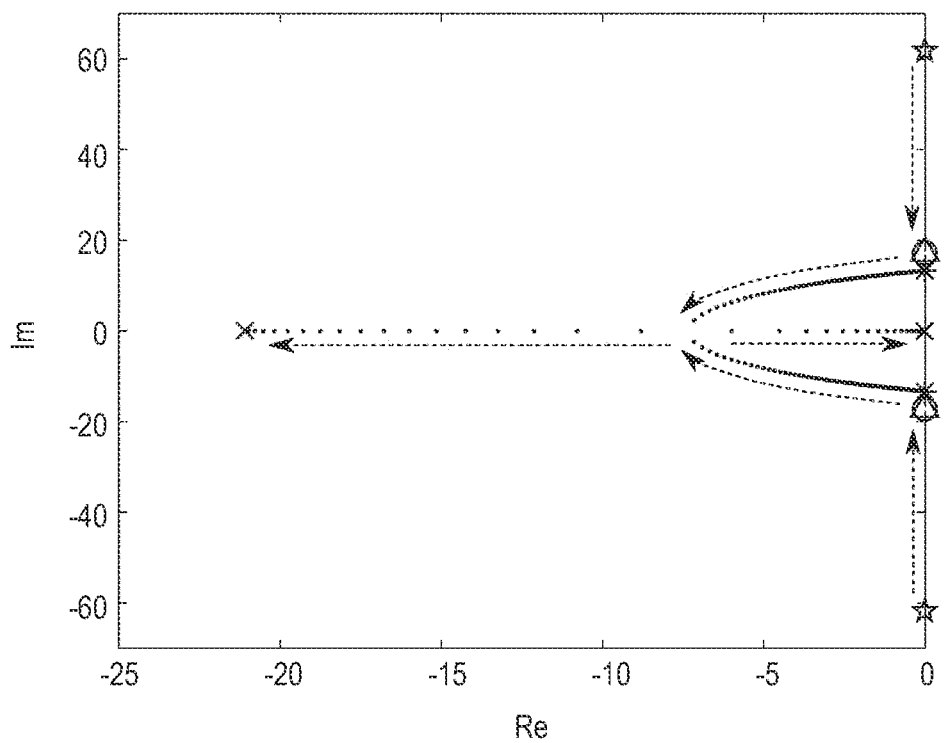
FIG. 4 shows an example of pole-zero response (pole-zero arrangement) of a dynamic model of the continuum robot according to the first embodiment of the present disclosure.

FIG. 4 is a diagram showing an example of poles-zeros response (poles-zeros arrangements) of the dynamic model $P_n$ of the continuum robot 100 according to the first embodiment of the present disclosure. In FIG. 4, the poles of the curvable unit 110 alone is indicated by a star, the poles and zeros at which the equivalent speed increasing ratio R is 10,000 times are indicated by an asterisk and a circle, respectively, and the poles and zeros at which the equivalent speed increasing ratio R is I time are indicated by an X and a triangle, respectively. As a result, it can be seen that the natural frequency of the curvable unit 110 decreases as the equivalent inertia on the motor side increases, and the pole of the curvable unit 110 moves to the overdamping poles and the origin poles. Note that the zeros indicated by the circles and triangles are not substantially moved. Although the frequency of the curvable unit 110 is overdamped, it is necessary to consider the phase characteristics in the control band due to the zeros in the control system design.

Figure 5:
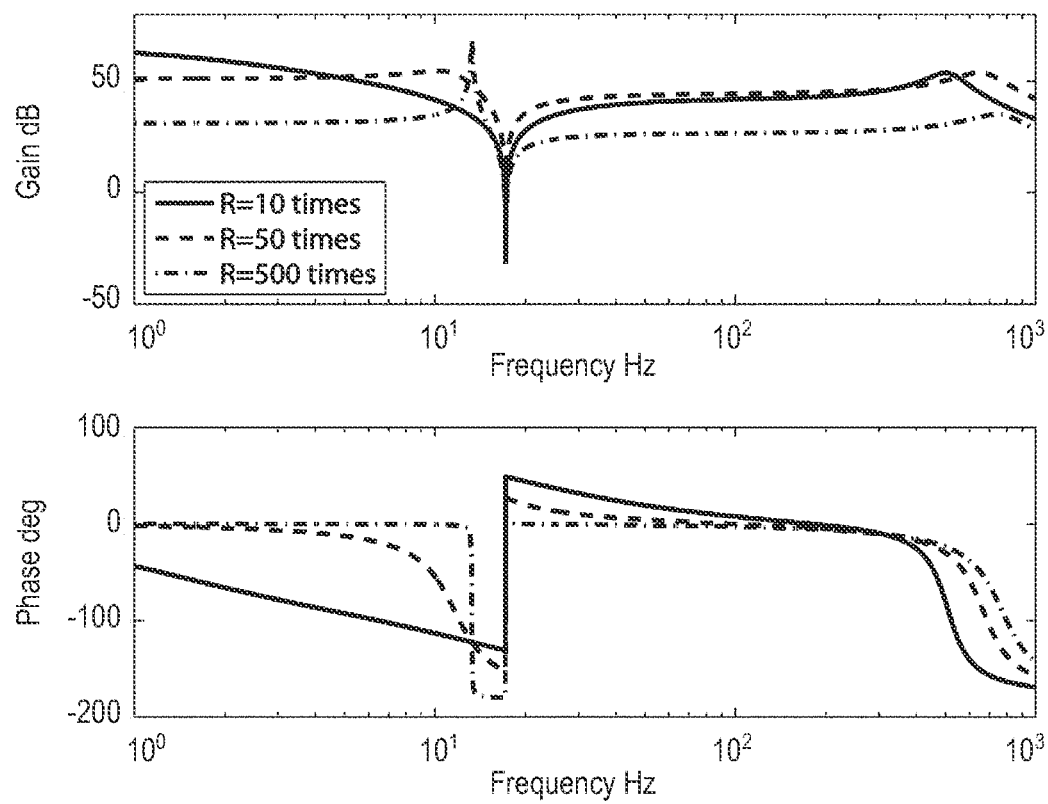
FIG. 5 is a Bode plot illustrating a dynamic model of the continuum robot according to the first embodiment of the present disclosure.

FIG. 5 is a Bode diagram showing the dynamic model $P_n$ of the continuum robot 100 according to the first embodiment of the present disclosure. Specifically, FIG. 5 shows a Bode diagram of an augmented system for varying the equivalent speed increasing ratio R. Here, in the augmented system, the equations (24) and (27) are linearized with the curving angle $\theta$ of 0.05 degrees. In FIG. 5, the transfer function from the motor target torque $T_m$, which is the control input, to the generated force F is shown, and the responses for the equivalent speed increasing ratio R of 10 times, 50 times, and 500 times are shown by solid lines, broken lines, and dashed dotted lines, respectively. It can be seen that as the equivalent speed increasing ratio R decreases and the equivalent inertia on the motor side increases, the peak of the continuum decreases and the anti-resonance frequency does not change. In the response in which the equivalent speed increasing ratio R shown by the solid line is multiplied by 10, it is difficult to understand the factor of the anti-resonance at about 18 Hz, but in the response in which the equivalent speed increasing ratio R shown by the broken line is multiplied by 500, it is understood that the anti-resonance is caused by the resonance and anti-resonance characteristics of the continuum portion in the augmented system in which the curvable unit 110 and the tension detection mechanism are combined. It can be seen that the phase leads by 180 degrees at this anti-resonance frequency.

Figure 6:
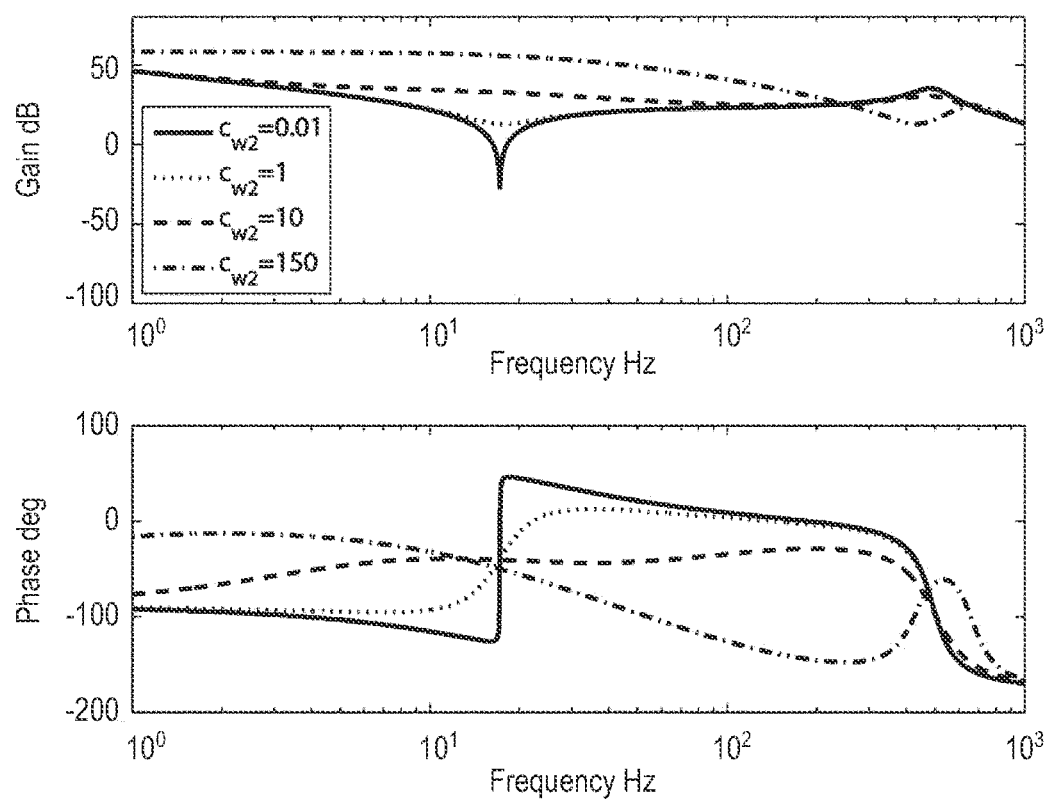
FIG. 6 is a Bode plot illustrating a dynamic model of the continuum robot according to the first embodiment of the present disclosure.

1.2.2) Variation for the Damping Coefficient $c_{w2}$ Due to Friction Between the Wire, and the Diameter Conversion Unit and the Wire Guide Next, the variation of the model by the damping coefficient $c_{w2}$ is examined. FIG. 6 is a Bode plot showing a dynamic model $P_n$ of the continuum robot 100 according to the first embodiment of the present disclosure. Specifically, FIG. 6 shows a Bode plot of an augmented system for varying the damping coefficient $c_{w2}$. In FIG. 6, the transfer functions from the motor torque $T_m$ which is the control input to the generated force F are shown, and the responses for setting the damping coefficient $c_{w2}$ to 0.01, 1, 10, and 150 are shown by solid lines, dotted lines, dashed lines, and dashed dotted lines, respectively. As the damping coefficient $c_{w2}$ increases, the low-frequency region changes from an integral characteristic to a first-order delay characteristic. Accordingly, the phase is inverted by 180 degrees around frequency of about 18 Hz on the zero. If this is in the vicinity of the target servo band, it greatly affects the design of the control system. In the control system design of the continuum robot 100-1 having the rotational linear motion conversion mechanism, it is understood that the model identification of the rotational linear motion conversion mechanism and the diameter conversion unit is important in addition to the natural frequency of the curvable unit 110.

Figure 7:
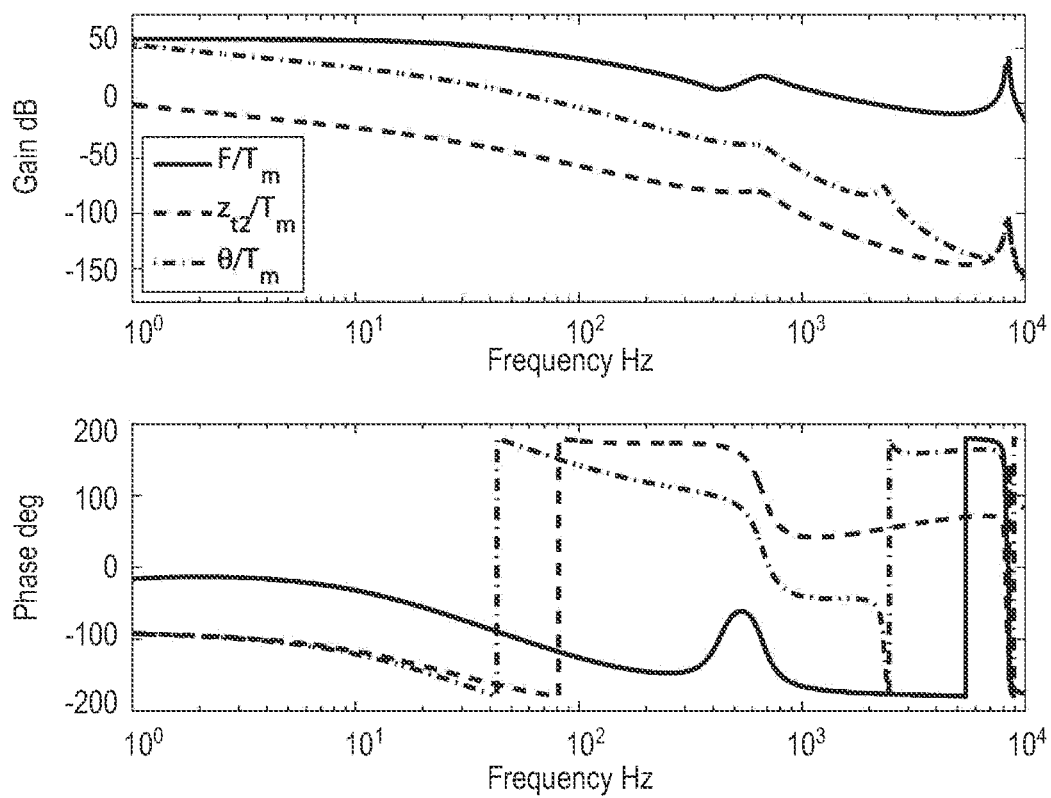
FIG. 7 is a Bode plot illustrating a dynamic model of the continuum robot according to the first embodiment of the present disclosure.

FIG. 7 is a Bode plot showing a dynamic model $P_n$ of the continuum robot 100 according to the first embodiment of the present disclosure. Specifically, FIG. 7 shows a Bode plot of an augmented system. The transfer function from the motor torque $T_m$ to the generated force F is indicated by a solid line, the transfer function from the motor torque $T_m$ to the displacement $z_{t2}$ of the wire holding mechanism is indicated by a broken line, and the transfer function from the motor torque $T_m$ to the curving angle θ of the curvable unit 110 is indicated by a dashed dotted line. In the high frequency region, high order vibration due to the spring and wire of the wire tension detection mechanism and rotational linear motion conversion mechanism appears.

1.3) Design of Control System

In this chapter, as shown in FIG. 1, the control system is designed by using a double loop control system having an inner loop control system (a first loop control system) including a force control unit $K_F$ and an outer loop control system (a second loop control system) including the force control unit Kr and a position control unit $K_{SV}$. The control system has a high back drivability with respect to the continuum robot 100-1 and realize high positioning performance of the curvable unit of the continuum robot 100 to the target position. Here, the dynamic model $P_n$ represents the augmented system shown in equations (24) and (27).

The relationship between the driving amount $l_p$ of the wire and the curving angle θ of the curvable unit 110 is given by the following equation (28).

$$l_p = r_1 \theta \quad (28)$$

In the present embodiment, because the amount of expansion and contraction of the wire is considered to be small, the amount of expansion and contraction of the wire is not considered in the derivation of the kinematics by the kinematics calculation unit 210. Therefore, the target displacement $\text{ref}_z$ is given by the following equation (29).

$$\text{ref}_z = r_1 \cdot \text{ref}_\theta \quad (29)$$

In the inner loop control system (the first loop control system) including the dynamic model $P_n$ of the augmented system and the force control unit $K_F$, an error is calculated by taking the difference between the target force $\text{ref}_F$, which is the target value of the generated force F, and the generated force F, and the force control unit $K_F$ outputs the motor torque $T_m$ as a control input for compensating the error. This feedback loop is equivalent to compensating for the equivalent inertia of the rotational linear motion conversion mechanism, thereby enabling improved back drivability of the continuum robot 100-1. In the present embodiment, as described above, the closed-loop system resulting from this feedback is referred to as $G_{cl}$. In the outer loop control system (the second loop control system) including the closed-loop control system $G_{cl}$ and the position control unit $K_{SV}$, an error is calculated by taking the difference between the target displacement $\text{ref}_z$ and the displacement 212 obtained from the continuum robot 100, and the position control unit $K_{SV}$ outputs the target generated force $\text{ref}_F$ as a control input for compensating the error.

In the present embodiment, as the inner loop control system (the first loop control system) for performing the force control, for example, a PI control system shown in the following equation (30) is used.

$$K_{PI}(s) = K_p\left(1 + \frac{K_i}{s}\right), K_i = 2\pi F_{zi} \quad (30)$$

where $F_{zi}$ is the zero crossing frequency of the integral controller. In addition, in order to stabilize the higher-order modes shown in the previous chapter, a second-order low-pass filter with a breakpoint frequency of 200 Hz is coupled to the PI control system. In order to design the stable force control unit $K_F$ for the variation of the poles and the zeros of the curvable unit 110 by using the rotational linear motion conversion mechanism and the phase characteristic varied by the damping coefficient $c_{w2}$ near the zeros, an open-loop transfer function $P_n K_F$ is derived and designed so that the gain margin and the phase margin are sufficient from the response (calculation of the stability margin is performed).

Figure 8A:
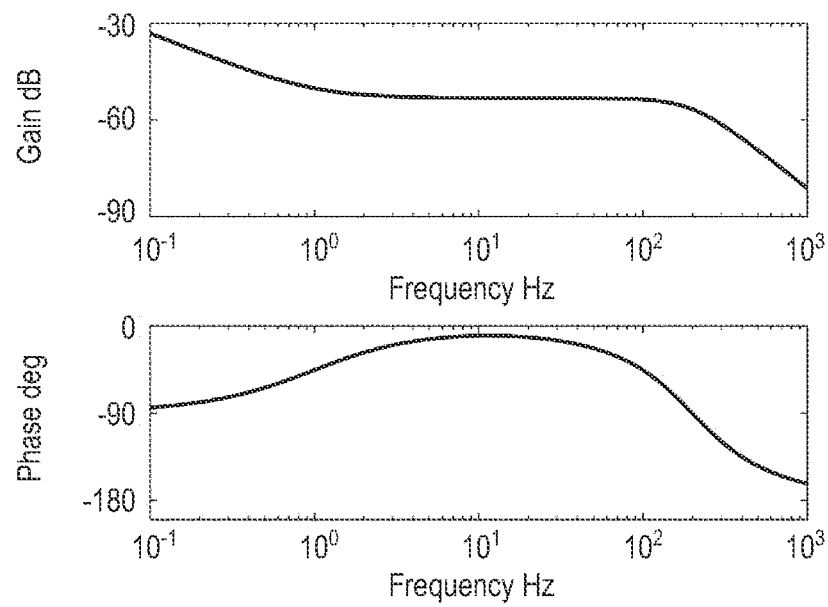
FIG. 8A is a Bode plot illustrating a force control unit of the continuum robot according to the first embodiment of the present disclosure.
Figure 8B:
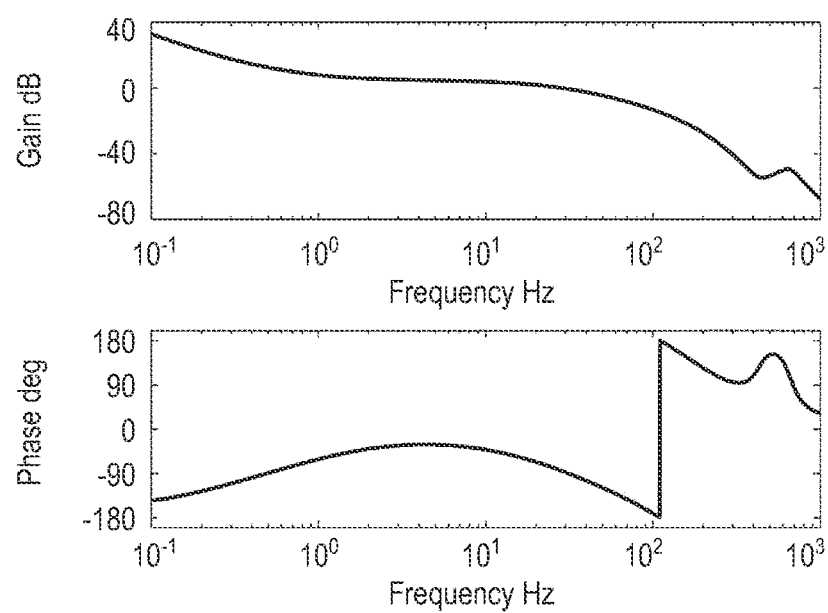
FIG. 8B is a Bode plot illustrating an open-loop transfer function of the continuum robot according to the first embodiment of the present disclosure.

FIGS. 8A and 8B are Bode plot showing a control apparatus 200 of a continuum robot according to the first embodiment of the present disclosure. Specifically, FIGS. 8A and 8B show a Bode plot of the force control unit $K_F$ in which $K_p$ and $F_{zi}$ of equations (30) of $2.2 \cdot 10^{-3}$ and 1.0, respectively, and a control band of about 30 Hz, and a Bode diagram of the open-loop transfer function $P_n K_F$ with the augmented system $P_n$.

In the present embodiment, as the outer loop control system (the second loop control system) for performing position control, for example, a PID control system shown in the following equation (31) is used.

$$K_{PID}(s) = K_p\left(1 + \frac{K_i}{s} + \frac{s}{K_d}\right), K_i = 2\pi F_{zi}, K_d = 2\pi F_{zd} \quad (31)$$

Here, $F_{zi}$ and $F_{zd}$ are zero crossing frequencies of the integral controller and the differential controller, respectively. An open-loop transfer function $G_{cl} K_{SV}$ is derived by using a closed-loop transfer function $G_{cl}$ between the dynamic model $P_n$ of the augmented system and the force control unit $K_F$, and designed so that a gain margin and a phase margin are sufficient from the response. A first order low-pass filter with a breakpoint frequency of 50 Hz is coupled to the PID control system.

Figure 9A:
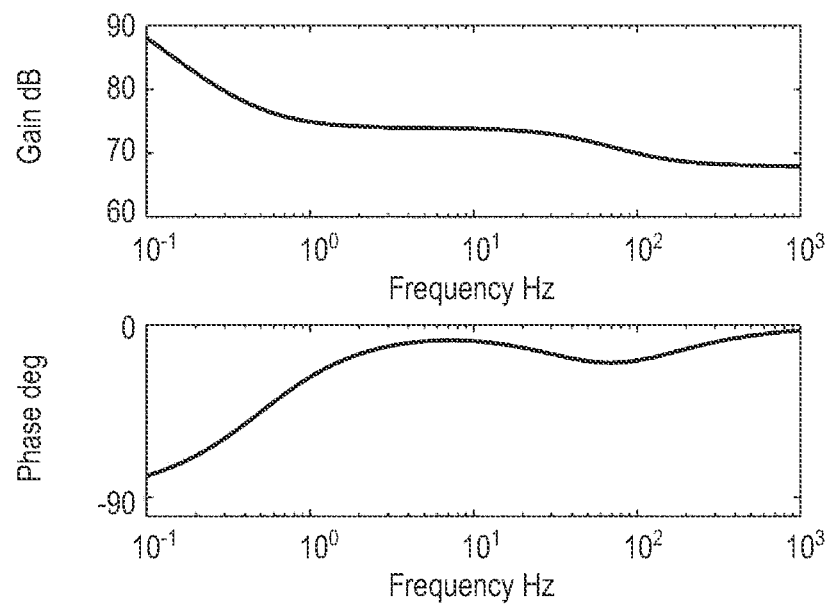
FIG. 9A is a Bode plot illustrating a position control unit of the continuum robot according to the first embodiment of the present disclosure.
Figure 9B:
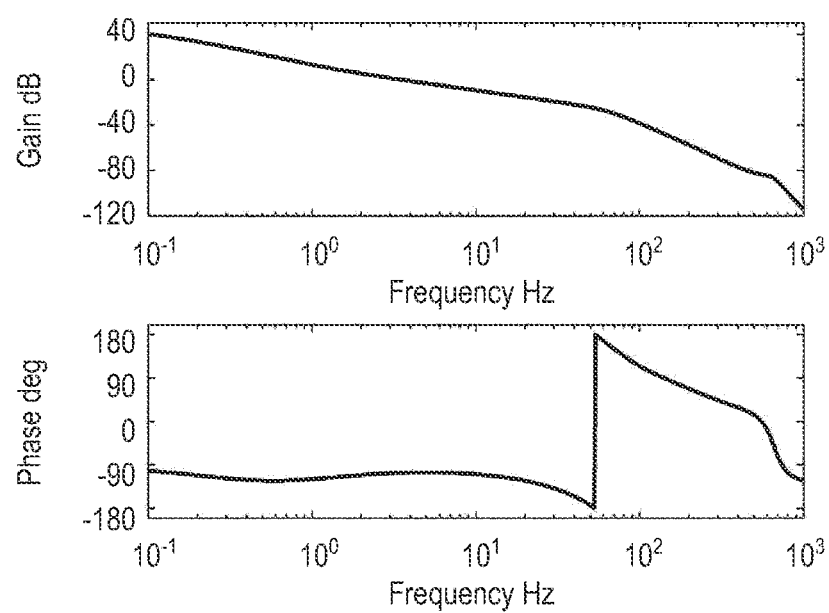
FIG. 9B is a Bode plot illustrating an open-loop system transfer function of the continuum robot according to the first embodiment of the present disclosure.

FIGS. 9A and 9B are Bode plots showing a control apparatus 200 of the continuum robot according to the first embodiment of the present disclosure. Specifically, FIGS. 9A and 9B show the Bode plots of the position control unit $K_{SV}$ in which $K_p$, $F_{zi}$, and $F_{zd}$ in equation (31) are 5-103, 0.5, and 100, respectively, and the control band is about 3.5 Hz, and the Bode plots of the open-loop transfer function $G_{cl} K_{SV}$ of the closed-loop control system $G_{cl}$ and the position control unit $K_{SV}$.

Figure 10:
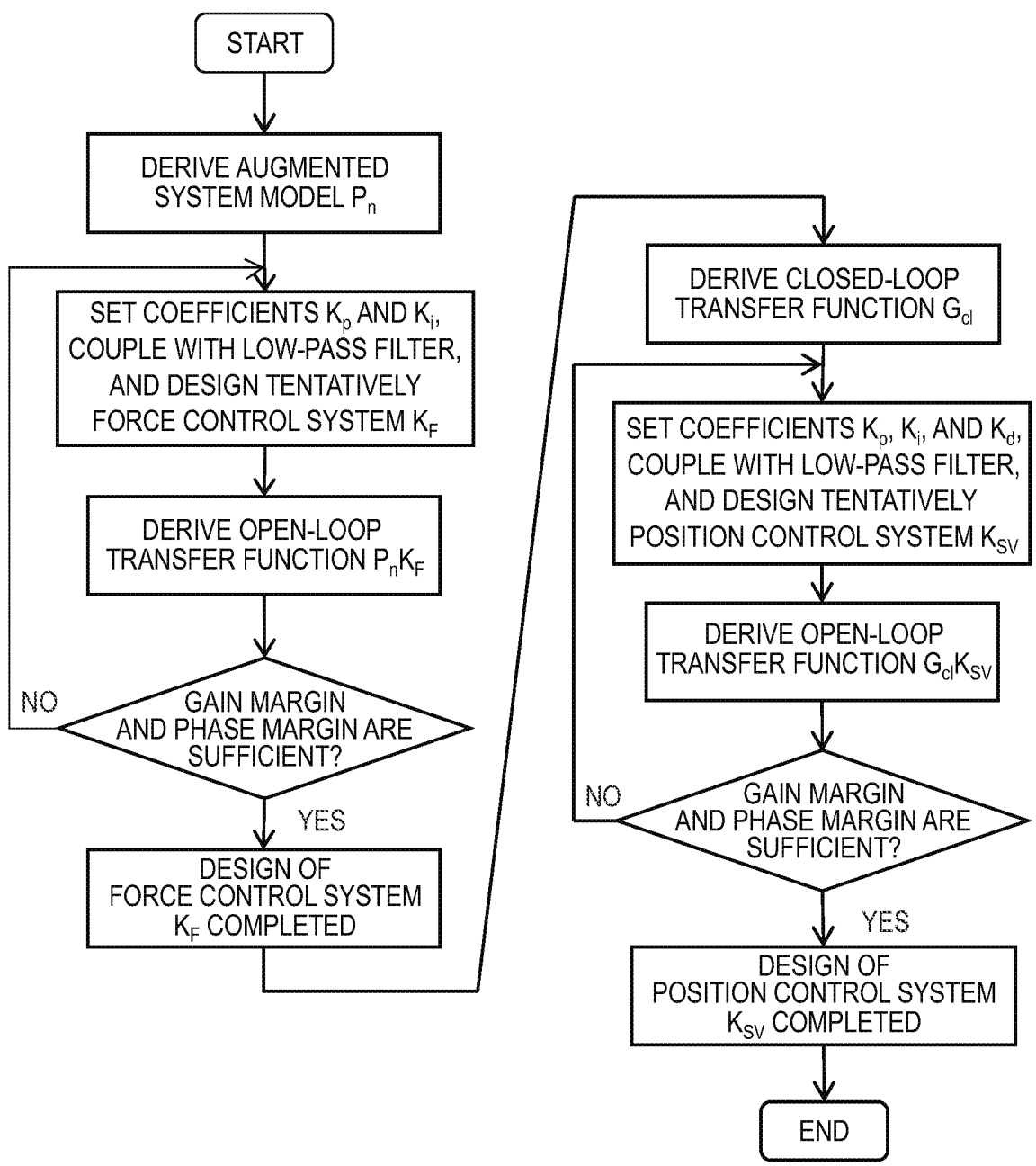
FIG. 10 is a flowchart showing a design procedure of a control system according to a control apparatus of the continuum robot according to the first embodiment of the present disclosure.

FIG. 10 is a flowchart showing a design procedure of a control system relating to the control apparatus 200 of the continuum robot according to the first embodiment of the present disclosure. FIG. 10 shows the following design procedure.

<1> Derive the dynamic model $P_n$ of the augmented system.

<2> Set the coefficients $K_p$ and $K_i$, couple with the low-pass filter, and design tentatively the force control unit $K_F$.

<3> Derive the open-loop transfer function $P_n K_F$.
<4> Determine whether or not the gain margin and phase margin are sufficient.
<5> Design of the force control unit $K_F$ completed.
<6> Derive the closed-loop system $G_{cl}$.
<7> Set the coefficients $K_p$, $K_i$, and $K_d$, couple with the low-pass filter, and design tentatively the position control unit $K_{SV}$.
<8> Derive the open-loop transfer function $G_{cl} K_{SV}$.
<9> Determine whether or not the gain margin and phase margin are sufficient.
<10> Design of the position control unit $K_{SV}$ completed.

1.4) Simulation

The simulation was carried out using the control system designed in (1.3) design of the control system and the augmented system shown in equations (24) and (27).

Figure 11A:
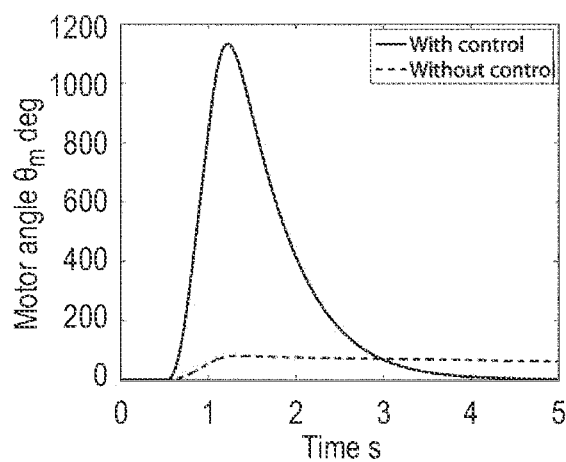
FIG. 11A shows a disturbance response to the rotation angle of a motor only in an inner loop control system (a first loop control system) using a force control unit according to the first embodiment of the present disclosure.
Figure 11B:
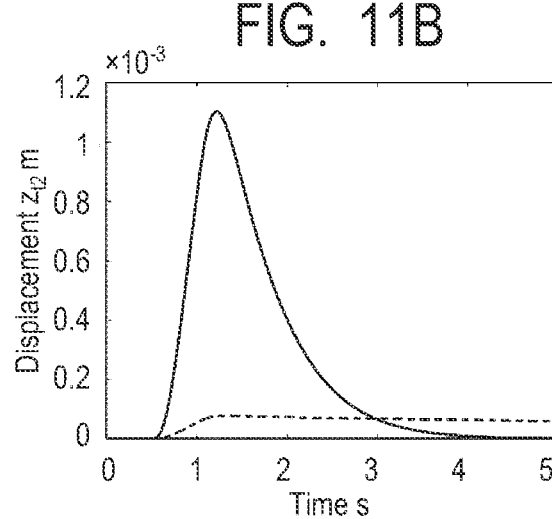
FIG. 11B shows a disturbance response to displacement of a wire holding mechanism only in an inner loop control system (a first loop control system) using a force control unit according to the first embodiment of the present disclosure.
Figure 11C:
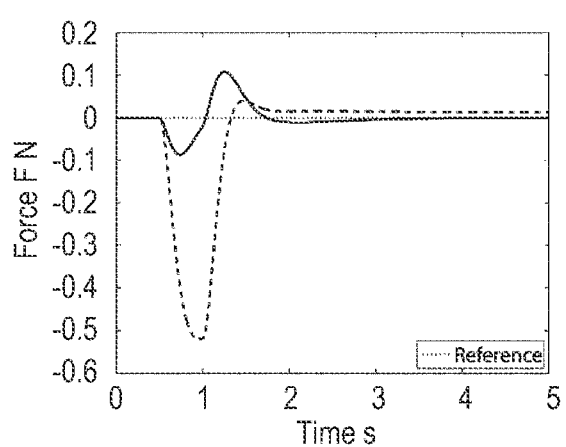
FIG. 11C shows a disturbance response with respect to a generated force only in an inner loop control system (a first loop control system) using a force control unit according to the first embodiment of the present disclosure.
Figure 11D:
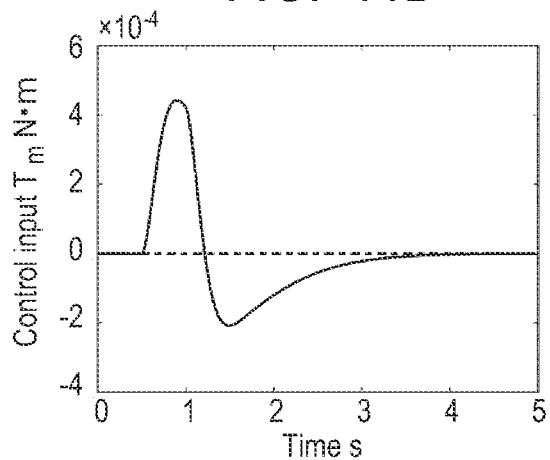
FIG. 11D shows a disturbance response to a control input only in an inner loop control system (a first loop control system) using a force control unit according to the first embodiment of the present disclosure.
Figure 11E:
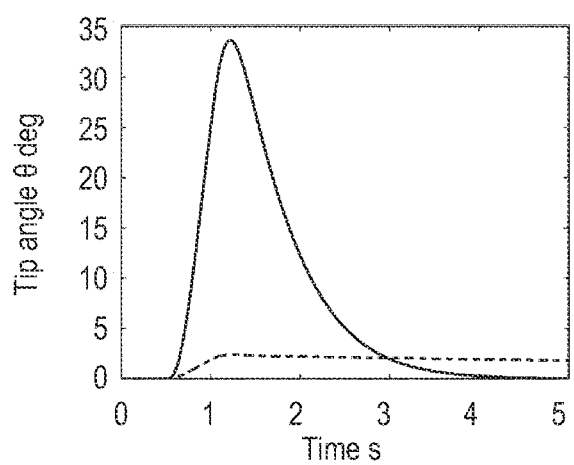
FIG. 11E shows a disturbance response to a curving angle only in an inner loop control system (a first loop control system) using a force control unit according to the first embodiment of the present disclosure.
Figure 11F:
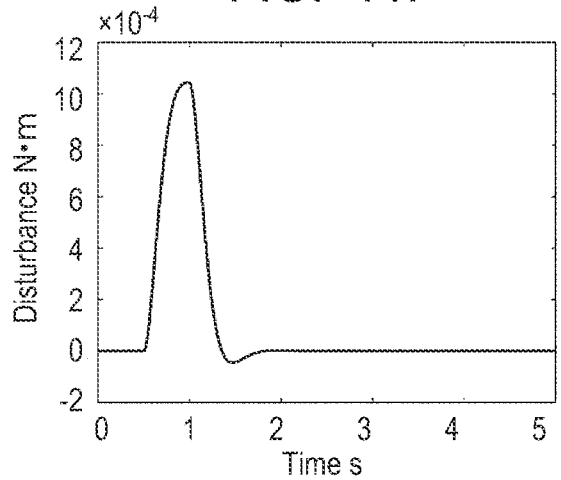
FIG. 11F shows disturbance response to disturbance torque only in an inner loop control system (a first loop control system) using a force control unit according to the first embodiment of the present disclosure.

FIGS. 11A to 11F show the first embodiment of the present disclosure, and show disturbance responses only of the inner loop control system (the first loop control system) using the force control unit $K_F$. Specifically, FIG. 11A shows the rotation angle $\theta_m$ of the motor, FIG. 11B shows the displacement $z_{t2}$ of the wire holding mechanism, FIG. 11C shows the generated force F, FIG. 11D shows the control input $T_m$, FIG. 11E shows the curving angle θ of the tip of the curvable unit 110, and FIG. 11F shows the disturbance torque applied to the tip of the curvable unit 110. In FIGS. 11A to 11F, the control response is indicated by a solid line, for comparison, the non-control response is indicated by a dashed line, and the target generated force $ref_F$ is indicated by a dotted line.

At 5 seconds after the start of the simulation, as shown in FIG. 11F, a disturbance torque is applied to the tip of the curvable unit 110. At this time, as shown in FIGS. 11A to 11F, a generated force in the negative z-axis direction acts on the wire holding mechanism by the spring of the tension detection mechanism, but the target value of the generated force F is 0. Therefore, as shown in FIG. 11D, the force control unit $K_F$ gives a positive control input to the motor, and when the motor rotates in the positive direction as shown in FIG. 11A, the wire holding mechanism is displaced in the positive direction of the z-axis as shown in FIG. 11B. As a result, as shown in FIG. 11C, the generated force F is compensated to 0, which is the target value, and as shown in FIG. 11E, the tip of the curvable unit 110 is curved in the same direction as the disturbance torque, and the motor is controlled to drive back in accordance with the disturbance torque. In the non-control response shown by the broken line, the disturbance torque shown in FIG. 11F is similarly applied, but because the equivalent inertia of the rotational linear motion conversion mechanism is large, the motor hardly rotates and the tip of the curvable unit 110 hardly curves, as shown by the broken line in FIGS. 11A and 11E. As a result, it can be seen that the inner loop control system for performing force control compensates for the equivalent inertia of the rotational linear motion conversion mechanism and enables the back drive against the disturbance torque of the end of the continuum.

Figure 12A:
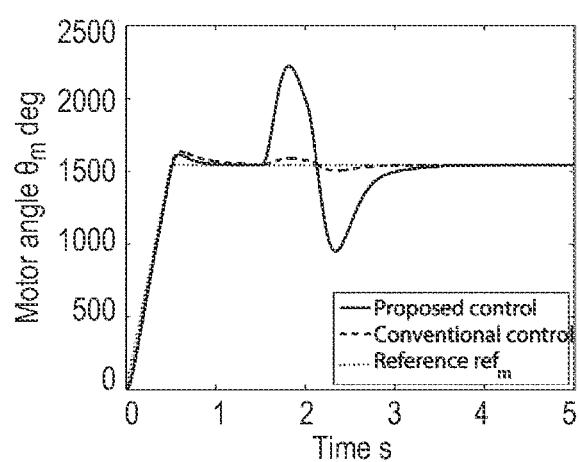
FIG. 12A shows a positioning response with disturbance to a motor rotation angle by a double-loop control system comprising an inner loop control system (a first loop control system) using a force control unit and an outer loop control system (a second loop control system) including a position control unit according to the first embodiment of the present disclosure.
Figure 12B:
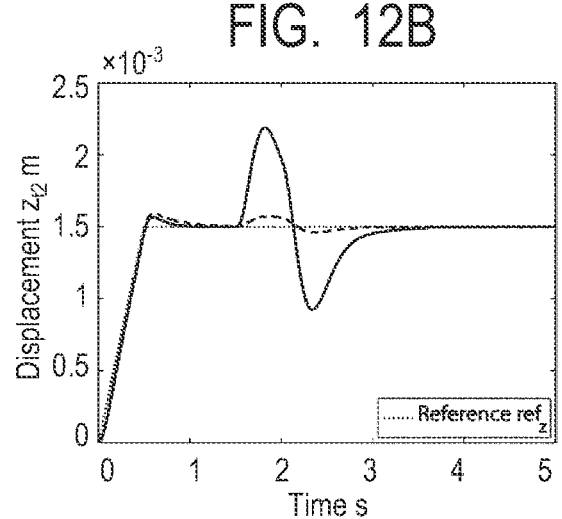
FIG. 12B shows a positioning response with disturbance to displacement of a wire holding mechanism by a double-loop control system comprising an inner loop control system (a first loop control system) using a force control unit and an outer loop control system (a second loop control system) including a position control unit according to the first embodiment of the present disclosure.
Figure 12C:
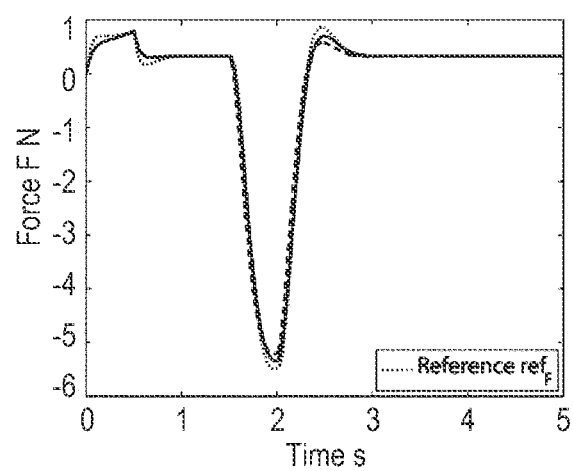
FIG. 12C shows a positioning response with disturbance to a generated force by a double-loop control system comprising an inner loop control system (a first loop control system) using a force control unit and an outer loop control system (a second loop control system) including a position control unit according to the first embodiment of the present disclosure.
Figure 12D:
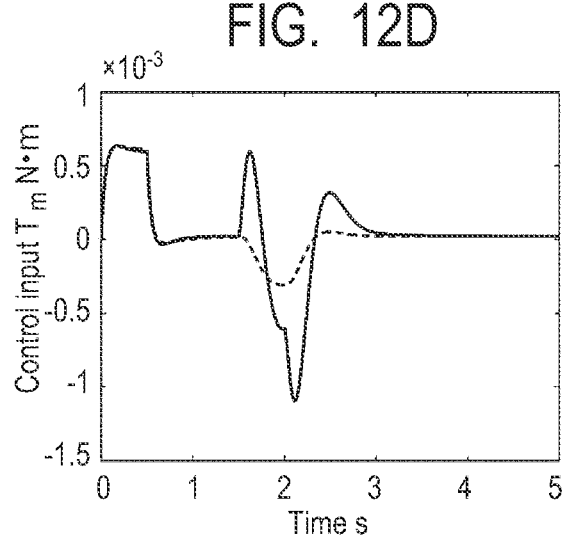
FIG. 12D shows a positioning response with disturbance to a control input by a double-loop control system comprising an inner loop control system (a first loop control system) using a force control unit and an outer loop control system (a second loop control system) including a position control unit according to the first embodiment of the present disclosure.

FIGS. 12A to 12F show the first embodiment of the present disclosure, and are diagrams showing positioning responses accompanied by disturbances by the double-loop control system comprising the inner loop control system (the first loop control system) using the force control unit $K_F$ and the outer loop control system (the second loop control system) further including the position control unit $K_{SV}$. Specifically, FIGS. 12A to 12F show the responses in the same arrangement as FIGS. 11A to 11F. This simulation shows a comparison with the semi-closed control in which the position control is performed by controlling only the rotation angle $\theta_m$ of the motor. The servo bands of the position control systems of the double-loop control system and the semi-closed control system are designed to be similar. In FIGS. 12A to 12F, the control response of the double-loop control system is indicated by a solid line, and the response of the semi-closed control system is indicated by a dashed line. FIG. 12A shows the target angle $ref_m$ of the motor applied to the semi-closed control system by a dotted line, FIG. 12B shows the target displacement $ref_z$ of the wire holding mechanism applied to the outer loop by a dotted line, and FIG. 12C shows the target generated force $ref_F$, which is the target value of the generated force F, which is the control input output by the position control unit $K_{SV}$, by a dotted line.

Figure 12E:
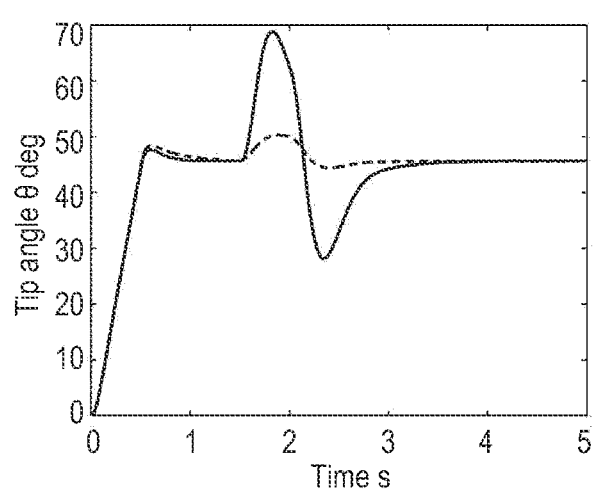
FIG. 12E shows a positioning response with disturbance to a curving angle by a double-loop control system comprising an inner loop control system (a first loop control system) using a force control unit and an outer loop control system (a second loop control system) including a position control unit according to the first embodiment of the present disclosure.
Figure 12F:
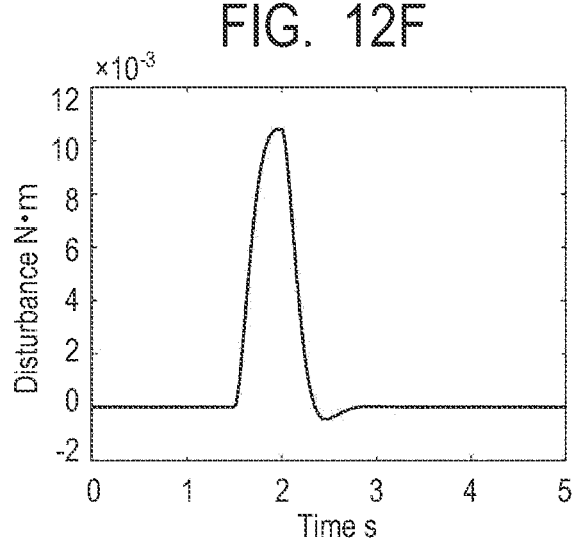
FIG. 12F shows a positioning response with disturbance to a disturbance torque by a double-loop control system comprising an inner loop control system (a first loop control system) using a force control unit and an outer loop control system (a second loop control system) including a position control unit according to the first embodiment of the present disclosure.

After the start of the simulation, both the double-loop control system and the semi-closed control system follow the target trajectory and are set to the target displacement in about one second. Thereafter, as shown in FIG. 12F, a disturbance torque is applied to the tip of the curvable unit 110 in 1.5 seconds. At this time, as shown in FIG. 12C, the position control unit $K_{SV}$ of the outer loop control system (the second loop control system) outputs the target value of the generated force in the negative z-axis direction as a control input in order to compensate for the displacement error generated in the displacement $z_{t2}$ of the wire holding mechanism. As shown in FIG. 12C, the force control unit $K_F$ of the inner loop control system (the first loop control system) follows the target generated force $ref_F$, which is the target value of the generated force F. However, since the equivalent inertia of the rotational linear motion conversion mechanism is compensated and reduced at the same time, the motor is backdriven in the positive direction as shown in FIG. 12A, and the wire holding mechanism is displaced in the positive z-axis direction as shown in FIG. 12B. The control input to the motor in the positive direction at 1.5 seconds in FIG. 12D indicates that the control to reduce the equivalent inertia is performed. As a result, as shown in FIG. 12E, it can be seen that the tip of the curvable unit 110 is curved in the same direction as the disturbance torque, thereby realizing a control system for backdriving against the disturbance torque. In the semi-closed control system shown by the broken line, when the disturbance torque of FIG. 12F is applied, the equivalent inertia of the rotational linear motion conversion mechanism is large, so that the motor hardly rotates and the tip of the curvable unit 110 hardly curves, as shown by the broken line in FIGS. 12A and 12E. Since the servo bands of the semi-closed control system and the double-loop control system are almost equal, the semi-closed control system is almost equal to the generated force F in FIG. 12F of the double-loop control system. Thus, it can be seen that the double-loop control system has the same setting performance to the target position as the semi-closed control system that controls the position by controlling only the rotation angle $\theta_m$ of the motor, and at the same time, enables the back drive to the disturbance torque at the tip of the curvable unit 110.

As described above, in the control system 10 of the continuum robot according to the first embodiment, the inner loop control system (the first loop control system) including the force control unit Kr and the outer loop control system (the second loop control system) including the force control unit Kr and the position control unit $K_{SV}$ are configured. According to this configuration, it is possible to realize high positioning performance of the curvable unit to the target position without requiring the operator to perform complicated operations. As a result, it is possible for the continuum robot 100 to have a high back drivability against disturbance at the tip of the curvable unit.

Second Embodiment

Next, a second embodiment of the present disclosure will be described. In the description of the second embodiment described below, matters common to the first embodiment described above will be omitted, and matters different from the first embodiment described above will be described.

In the first embodiment described above, it has been shown that the curvable unit 110, which is a continuum portion, is coupled with the rotational linear motion conversion mechanism, so that the vibration characteristics move to a low frequency range, and that the phase characteristics vary due to friction between the wire, the diameter conversion unit, and the wire guide. In the first embodiment described above, the PI control system is used as the force control unit $K_F$ of the inner loop control system (the first loop control system) that performs force control.

On the other hand, in the second embodiment, the phase characteristic is compensated by using a PID control system in the force control unit $K_F$. Here, for example, the PID control system shown in equation (32) below is used.

$$K_{PID}(s) = K_P\left(1 + \frac{K_i}{s} + \frac{s}{K_d}\right), K_i = 2\pi F_{zi}, K_d = 2\pi F_{zd} \quad (32)$$

Here, $F_{zi}$ and $F_{zd}$ are zero crossing frequencies of the integral controller and the differential controller, respectively. A second-order low-pass filter having a breakpoint frequency of 200 Hz is coupled (for example, series-coupled) to the PID control system (a PID control unit). As in the first embodiment, the open-loop transfer function $P_n K_F$ is derived and designed so that the gain margin and the phase margin are sufficient from the response thereof. In the second embodiment, a method for designing the gain $K_d$ is shown. In the PID control system, the differential controller can lead the phase without increasing the gain (differential gain) at frequencies lower than the zero crossing frequency $F_{zd}$. However, the gain is raised at a frequency higher than $F_{zd}$. Therefore, the zero crossing frequency $F_{zd}$ is changed, and the gain margin is calculated (the stability margin is calculated) by using the open-loop transfer function $P_n K_F$ each time, so that the relationship between the zero crossing frequency $F_{zd}$ and the gain margin is acquired, and the zero crossing frequency $F_{zd}$ for maximizing the gain margin is searched.

Figure 13:
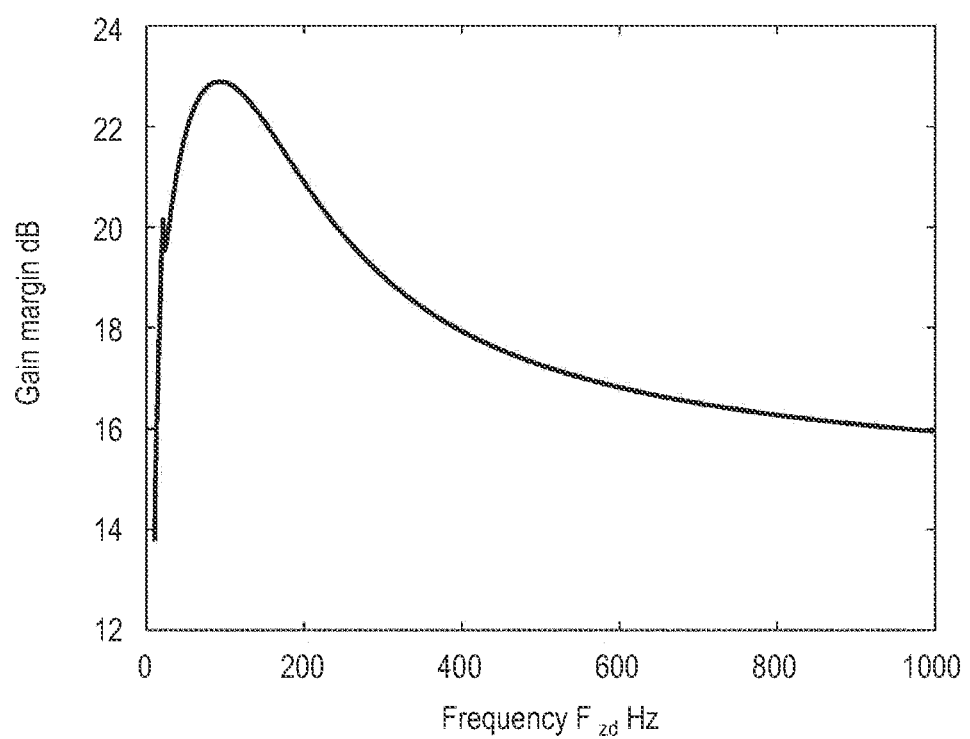
FIG. 13 shows a parameter search of a control system according to a control apparatus of the continuum robot according to a second embodiment of the present disclosure.

FIG. 13 is a diagram showing a parameter search of the control system relating to the control apparatus 200 of the continuum robot according to the second embodiment of the present disclosure. Specifically, FIG. 13 shows the response of the gain margin search in which the minimum frequency is set to 1 Hz which is sufficiently lower than the zero of the curvable unit 110 which is the continuum portion shown in the first embodiment, and the maximum frequency is set to, for example, 1 kHz which is the Nyquist frequency when the control system is digitally implemented. In FIG. 13, it can be seen that the gain margin becomes maximum at around 95 Hz of the zero crossing frequency $F_{zd}$.

Figure 14A:
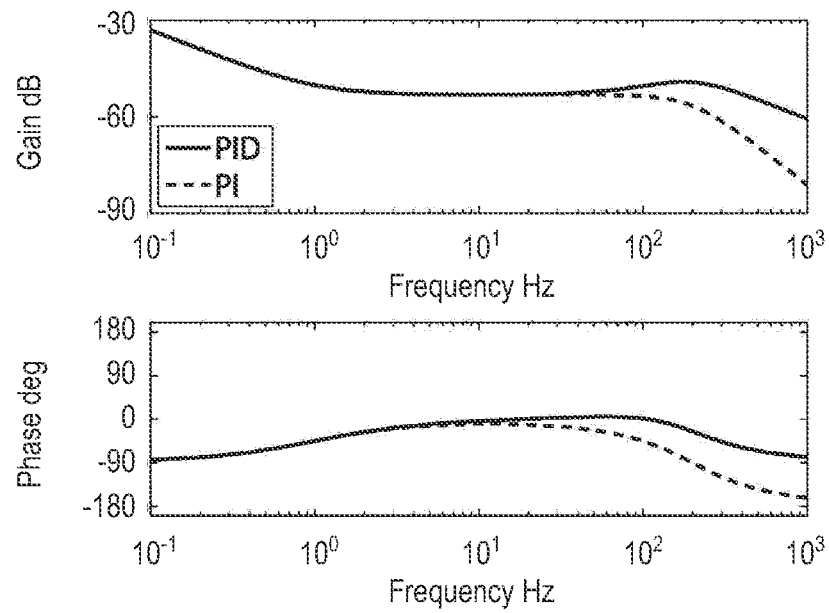
FIG. 14A is a Bode plot showing a force control unit according to a control apparatus of the continuum robot according to the second embodiment of the present disclosure.
Figure 14B:
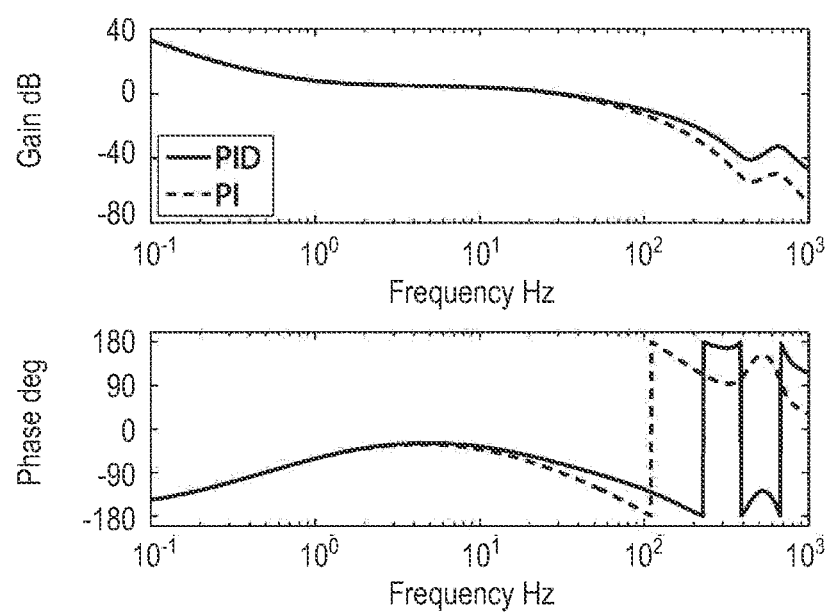
FIG. 14B is a Bode plot showing an open-loop transfer function according to a control apparatus of the continuum robot according to a second embodiment of the present disclosure.

FIGS. 14A and 14B are diagrams showing a Bode plot and an open-loop response of a control system according to a control apparatus 200 of a continuum robot according to the second embodiment of the present disclosure. Specifically, FIG. 14A shows a Bode plot of the PID control system of the force control unit $K_F$, and FIG. 14B shows a Bode plot of the open-loop transfer function $P_n K_F$. In FIGS. 14A and 14B, the case of the PID control system of the second embodiment in which the zero crossing frequency $F_{zd}$ is 95 Hz is shown by a solid line, and the case of the PI control system of the first embodiment is shown by a broken line. The open-loop response shows that the gain margin is improved by approximately 7 dB by compensating the phase delay with the differential characteristics.

Figure 15:
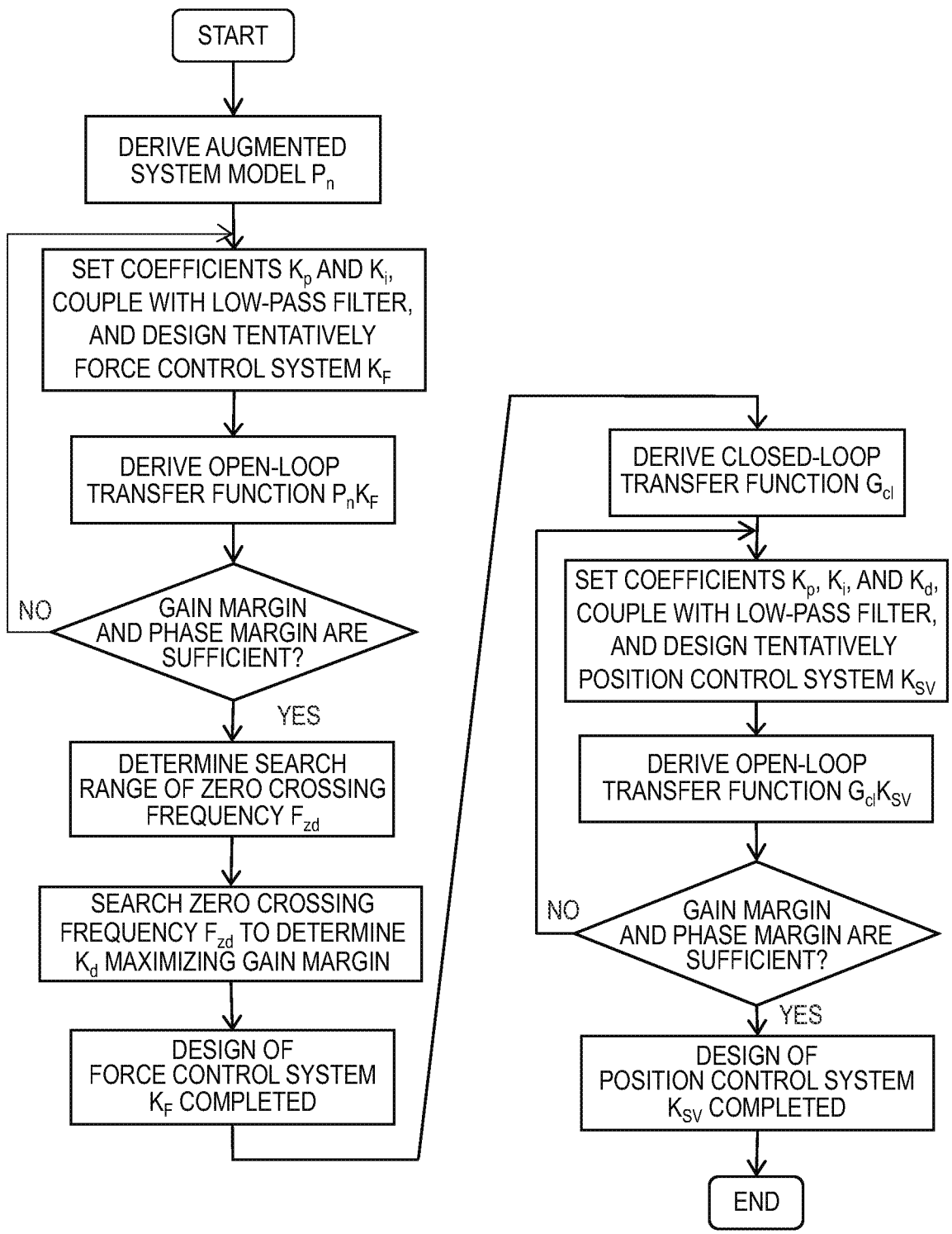
FIG. 15 is a flowchart showing a design procedure of a control system according to a control apparatus of the continuum robot according to the second embodiment of the present disclosure.

FIG. 15 is a flowchart showing a design procedure of the control system relating to the control apparatus 200 of the continuum robot according to the second embodiment of the present disclosure. FIG. 15 shows the following design procedure.

<1> Derive the dynamic model $P_n$ of the augmented system.
<2> Set the coefficients $K_p$ and $K_i$, couple with the low-pass filter, and design tentatively the force control unit $K_F$.
<3> Derive the open-loop transfer function $P_n K_F$.
<4> Determine whether or not the gain margin and phase margin are sufficient.
<5> Determine the search range of the zero crossing frequency $F_{zd}$.
<6> Search the zero crossing frequency $F_{zd}$ to determine $K_d$ maximizing the gain margin.
<7> Design of the force control unit $K_F$ completed.
<8> Derive the closed-loop system $G_{cl}$.
<9> Set the coefficients $K_p$, $K_i$, and $K_d$, couple with the low-pass filter, and design tentatively the position control unit $K_{SV}$.
<10> Derive the open-loop transfer function $G_{cl} K_{SV}$.
<11> Determine whether or not the gain margin and phase margin are sufficient.
<12> Design of the position control unit $K_{SV}$ completed.

Third Embodiment

Next, a third embodiment of the present disclosure will be described. In the description of the third embodiment described below, matters common to the first and second embodiments described above will be omitted, and matters different from the first and second embodiments described above will be described.

In the second embodiment described above, the phase delay characteristic is compensated by the differential element of the PID control system. In the third embodiment, the order of the control system is increased and the phase delay is compensated. The gain of the inner loop control system (the first loop control system) for performing force control is increased to broad the control band of the inner loop control system so as to correspond to the improved gain margin. Then, the effectiveness is verified by simulation.

3.1) Design of Control System

A phase lead filter represented by the following equation (33) is coupled (for example, series coupling) to the force control unit $K_F$ designed in the above-described second embodiment. In the present embodiment, it is referred to as a PID-Lead control system.

$$F_L(s) = \frac{s/F_{c1} 1}{s/F_{c2} 1} \quad (33)$$

Here, $F_{c1}$ is a zero crossing frequency, and $F_{c2}$ ($>F_{c1}$) is a pole for making the filter a proper. In the present embodiment, $F_{c2}$ is set to 1 kHz, and $F_{c1}$ is searched. Similarly to the second embodiment, the zero crossing frequency $F_{c1}$ is changed and the relationship between the zero crossing frequency $F_{c1}$ and the gain margin is acquired by computing the gain margin each time, and the zero crossing frequency $F_{c1}$ with the maximum gain margin is searched.

Figure 16:
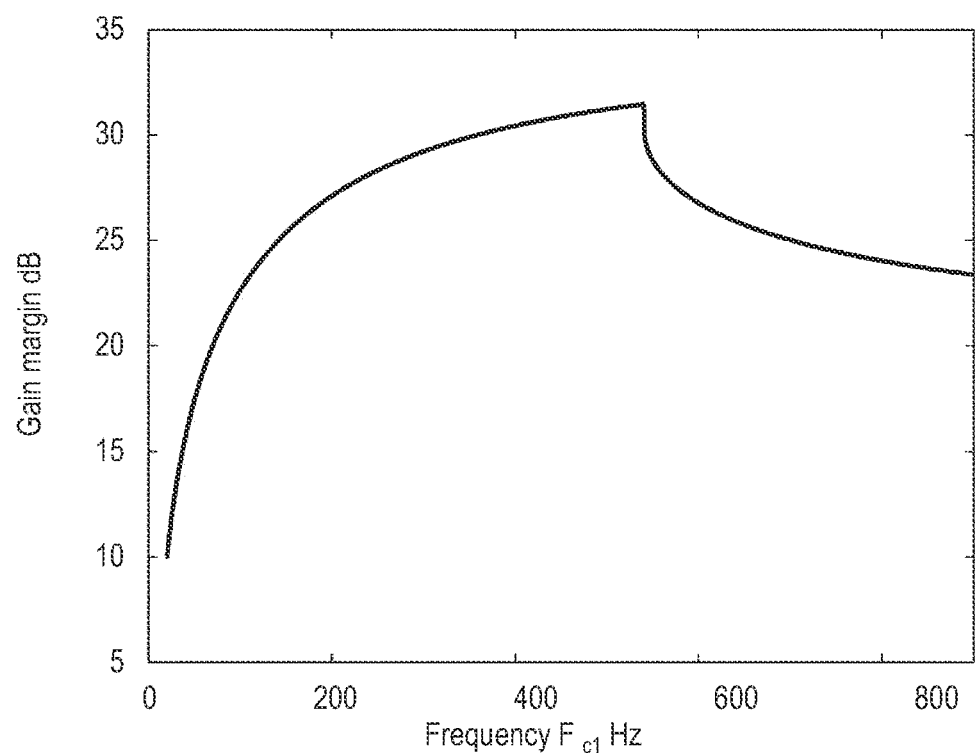
FIG. 16 shows a parameter search of a control system according to a control apparatus of the continuum robot according to the third embodiment of the present disclosure.

FIG. 16 is a diagram showing a parameter search of the control system relating to the control apparatus 200 of the continuum robot according to the third embodiment of the present disclosure. Specifically, FIG. 16 shows a search response in which the minimum frequency is set to 1 Hz, which is sufficiently lower than the zeros of the curvable unit 110, which is a continuum portion, and the maximum frequency is set to 900 Hz, which is equal to or lower than the maximum frequency $F_{c2}$. In FIG. 16, it can be seen that the gain margin becomes maximum at around 540 Hz of the zero crossing frequency $F_{c1}$. Since the response is steep, the gain margin is improved by about 6 dB when the zero crossing frequency $F_{c1}$ is set to 545 Hz with a slight margin.

Figure 17A:
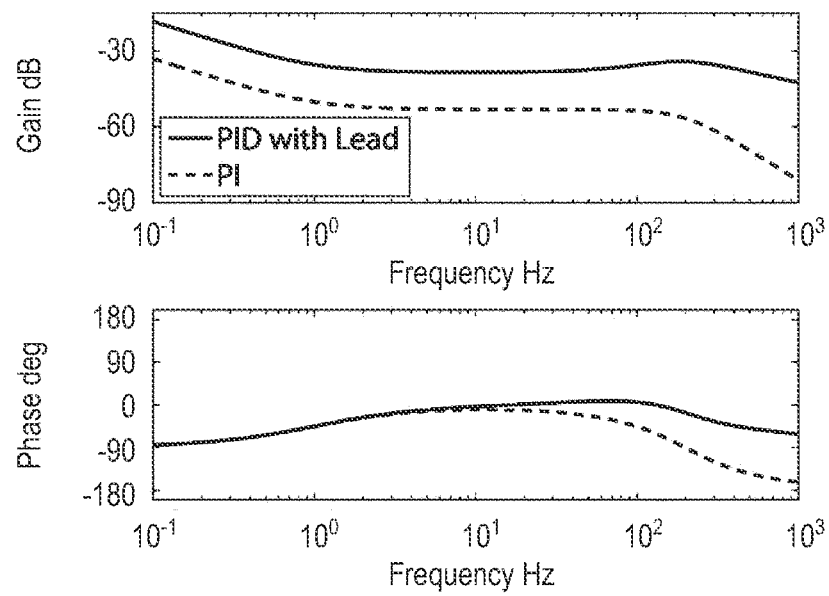
FIG. 17A is a Bode plot showing a force control unit according to a control apparatus of the continuum robot according to the third embodiment of the present disclosure.
Figure 17B:
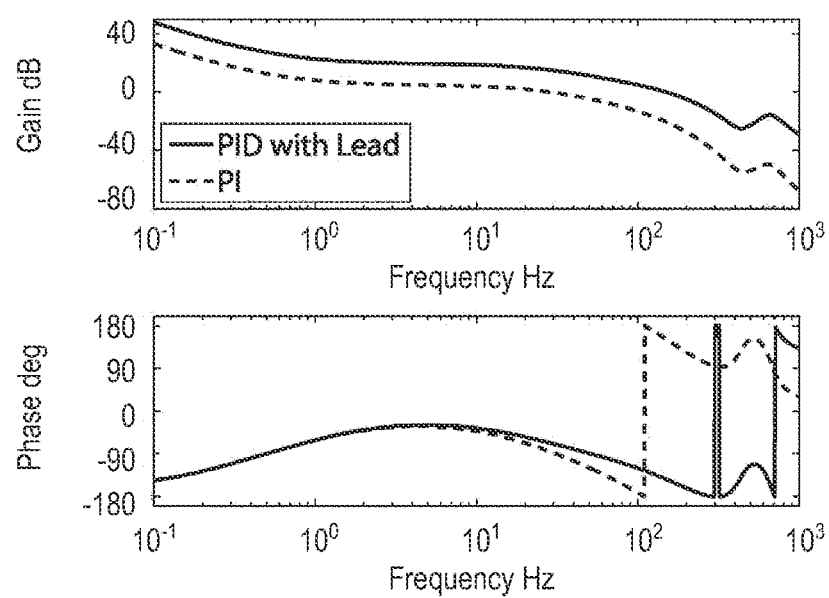
FIG. 17B is a diagram showing a Bode diagram of an open-loop transfer function according to a control apparatus of the continuum robot according to the third embodiment of the present disclosure.

FIGS. 17A and 17B are diagrams showing a Bode plot and an open-loop response of a control system according to a control apparatus 200 of a continuum robot according to the third embodiment of the present disclosure. Specifically, FIG. 17A is a Bode plot of the PID-Lead control system of the force control unit $K_F$, and FIG. 17B is a Bode plot of the open-loop transfer function $P_n K_F$. In FIGS. 17A and 17B, the force control system using the PID-Lead control system is shown by a solid line, and a control system of the first embodiment is shown by a broken line. Here, the PID-Lead control system increases the gain by 13 dB, which corresponds to an improved gain margin from the PI control system of the first embodiment. Therefore, the gain is higher than that of the control system of the first embodiment, but the gain margin is equal.

FIG. 18 is a flowchart showing a design procedure of the control system relating to the control apparatus 200 of the continuum robot according to the third embodiment of the present disclosure. FIG. 18 shows the following design procedure.

<1> Derive the dynamic model $P_n$ of the augmented system.
<2> Set the coefficients $K_p$ and $K_i$, couple with the low-pass filter, and design tentatively the force control unit $K_F$.
<3> Derive the open-loop transfer function $P_n K_F$.
<4> Determine whether or not the gain margin and phase margin are sufficient.
<5> Store the gain margin GM1.
<6> Determine the search range of the zero crossing frequency $F_{zd}$.
<7> Search the zero crossing frequency $F_{zd}$ to determine the $K_d$ maximizing the gain margin.
<8> Determine the search range of the frequency $F_{c1}$ of the phase lead filter and the frequency $F_{c2}$.
<9> Search the frequency $F_{c1}$ to determine the phase lead filter with the maximum gain margin.
<10> Store the gain margin GM2.
<11> Multiply the tentatively designed force control system $K_F$ by the gain equivalent to GM2−GM1.
<12> Design of the force control unit $K_F$ completed.
<13> Derive the closed-loop system $G_{cl}$.
<14> Set the coefficients $K_p$, $K_i$, and $K_d$, couple with the low-pass filter, and design tentatively the position control unit $K_{SV}$.
<15> Derive the open-loop transfer function $G_{cl} K_{SV}$.
<16> Determine whether or not the gain margin and phase margin are sufficient.
<17> Design of the position control unit $K_{SV}$ completed.

3.2) Simulation

Figure 19A:
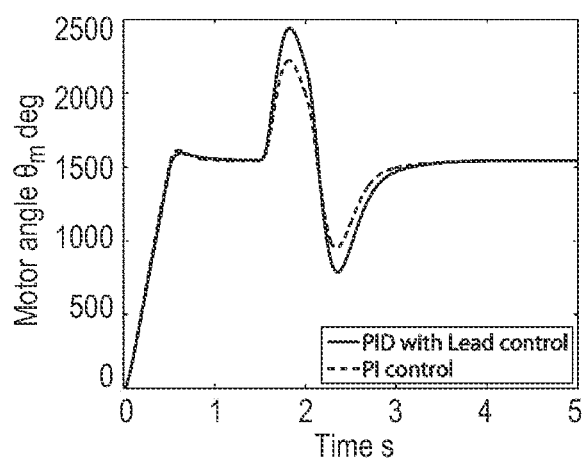
FIG. 19A shows a positioning response with disturbance to a rotation angle of a motor by a double-loop control system comprising an inner loop control system (a first loop control system) using a force control unit and an outer loop control system (a second loop control system) including a position control unit according to the third embodiment of the present disclosure.
Figure 19B:
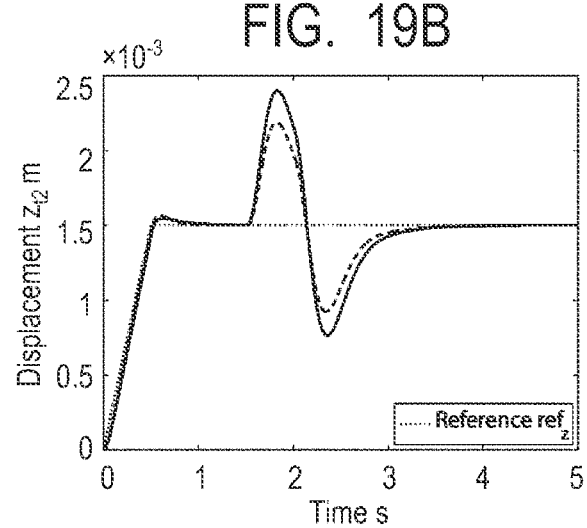
FIG. 19B shows a positioning response with disturbance to displacement of a wire holding mechanism by a double-loop control system between an inner loop control system (a first loop control system) using a force control unit and an outer loop control system (a second loop control system) including a position control unit according to the third embodiment of the present disclosure.
Figure 19C:
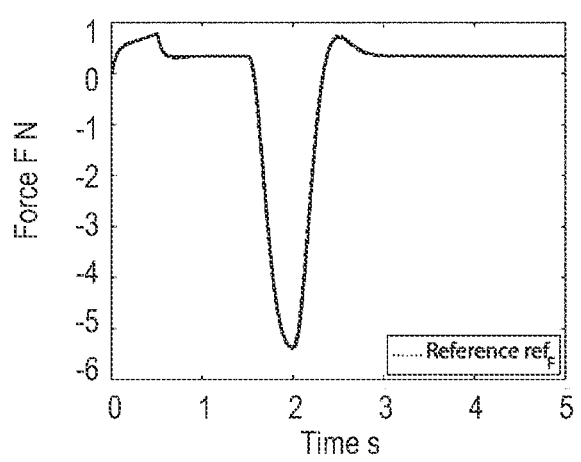
FIG. 19C shows a positioning response with a disturbance to a generated force by a double-loop control system of an inner loop control system (a first loop control system) using a force control unit and an outer loop control system (a second loop control system) including a position control unit according to the third embodiment of the present disclosure.
Figure 19D:
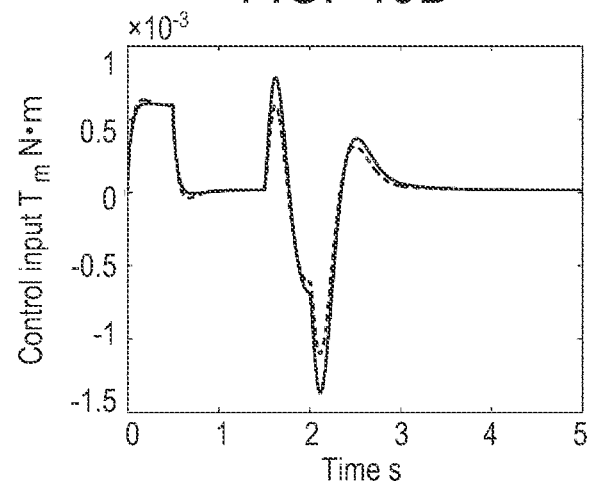
FIG. 19D shows a positioning response with disturbance to a control input by a double-loop control system between an inner loop control system (a first loop control system) using a force control unit and an outer loop control system (a second loop control system) including a position control unit according to the third embodiment of the present disclosure.

FIGS. 19A to 19F show the third embodiment of the present disclosure, and are diagrams showing positioning responses accompanied by disturbances by the double-loop control system comprising the inner loop control system (the first loop control system) using the force control unit $K_F$ and the outer loop control system (the second loop control system) further including the position control unit $K_{SV}$. Specifically, FIGS. 19A to 19F show the responses in the same arrangement as FIGS. 11A to 11F. This simulation shows a comparison with the PI control system of the first embodiment. The servo band of the outer loop control system (the second loop control system) of the double-loop control system using the PID-Lead control system is designed to be similar to that of the first embodiment. In FIGS. 19A to 19F, the response of the PID-Lead control system is indicated by a solid line, and the response of the PI control system is indicated by a dashed line. FIG. 19B shows the target displacement $ref_z$ of the wire holding mechanism applied to the outer loop as a dotted line, and FIG. 19C shows the target generated force $ref_F$ as a control input output from the position control unit $K_{SV}$ as a dotted line.

Figure 19E:
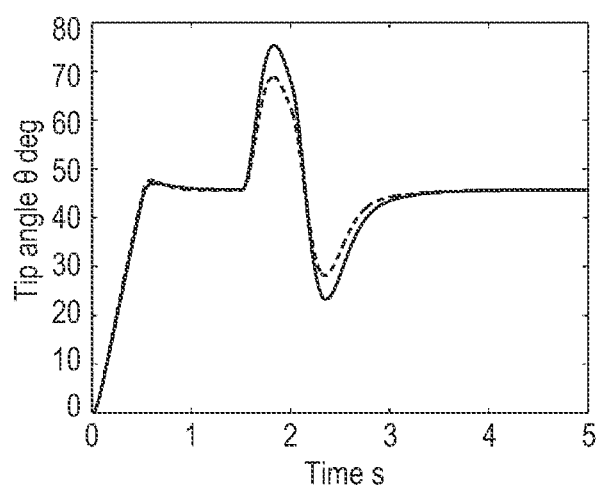
FIG. 19E shows a positioning response with disturbance to a curving angle by a double-loop control system between an inner loop control system (a first loop control system) using a force control unit and an outer loop control system (a second loop control system) including a position control unit according to the third embodiment of the present disclosure.
Figure 19F:
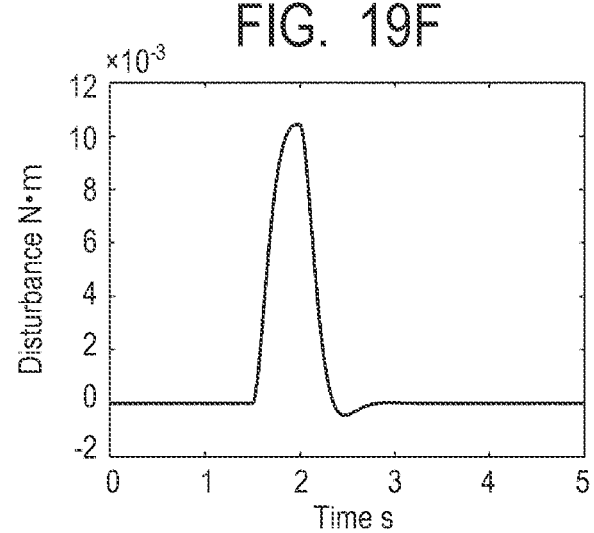
FIG. 19F shows a positioning response with disturbance to a disturbance torque by a double-loop control system of an inner loop control system (a first loop control system) using a force control unit and an outer loop control system (a second loop control system) including a position control unit according to the third embodiment of the present disclosure.

After the start of the simulation, both the PID-Lead control system and the PI control system follow the target trajectory and set to the target displacement in about one second. Thereafter, as shown in FIG. 19F, a disturbance torque is applied to the tip of the curvable unit 110 in 1.5 seconds. As in the first embodiment, as shown in FIG. 19C, the position control unit $K_{SV}$ of the outer loop control system (the second loop control system) outputs the target generated force $ref_F$, which is the target value of the generated force F in the negative z-axis direction, as a control input, and the force control unit $K_F$ of the inner loop control system (the first loop control system) follows the target value of the generated force F. Since the force control unit $K_F$ simultaneously compensates and reduces the equivalent inertia of the rotational linear motion conversion system, the motor is driven back in the positive direction as shown in FIG. 19A, and the wire holding mechanism is extended in the positive z-axis direction as shown in FIG. 19B. Here, it can be seen that the PID-Lead control system has a higher gain than the PI control system, and therefore is largely back-driven. From the control input to the motor shown in FIG. 19D, it can be seen that the PID-Lead control system has a larger control input to reduce the equivalent inertia than the PI control system. As a result, as shown in FIG. 19E, the PID-Lead control system realizes control with a large back drivability against the disturbance torque to the tip of the curvable unit 110. The PID-Lead control system is also stable to higher-order vibration modes.

Since the PID-Lead control system can design the force control unit $K_F$ of the inner loop control system (the first loop control system) to be high gain by compensating the phase delay characteristic at a higher order, the equivalent inertia of the rotational linear motion conversion mechanism can be compensated to be high gain, and the back drivability can be increased.

Fourth Embodiment

Next, a fourth embodiment of the present disclosure will be described. In the description of the fourth embodiment described below, matters common to the first to third embodiments described above will be omitted, and matters different from the first to third embodiments described above will be described.

In the first and second embodiments described above, it has been shown that the double-loop control system can provide back drivability to the continuum robot 100. Furthermore, in the third embodiment, it has been shown that back drivability can be increased by designing the force control unit $K_F$ of the inner loop control system (the first loop control system) to be high gain. The present embodiment shows a control system capable of adjusting the magnitude of the back drivability without changing the positioning performance.

First, as shown in the first to third embodiments, the double-loop control system is designed. The force control unit $K_F$ is multiplied by a coefficient (a first coefficient) $\alpha$ of 0 to 1. Thus, the gain of the force control unit Kr is lowered, and the magnitude of the back drivability can be arbitrarily reduced. However, since the gain of the open-loop transfer function $G_{cl}K_{SV}$ simultaneously decreases, the servo band of the positioning control decreases. Therefore, the gain of the position control unit $K_{SV}$ is increased, and the servo band is redesigned so as to be the same as when the coefficient $\alpha$ is 1. Thus, the back drivability can be varied without changing the performance of the position control.

Figure 20A:
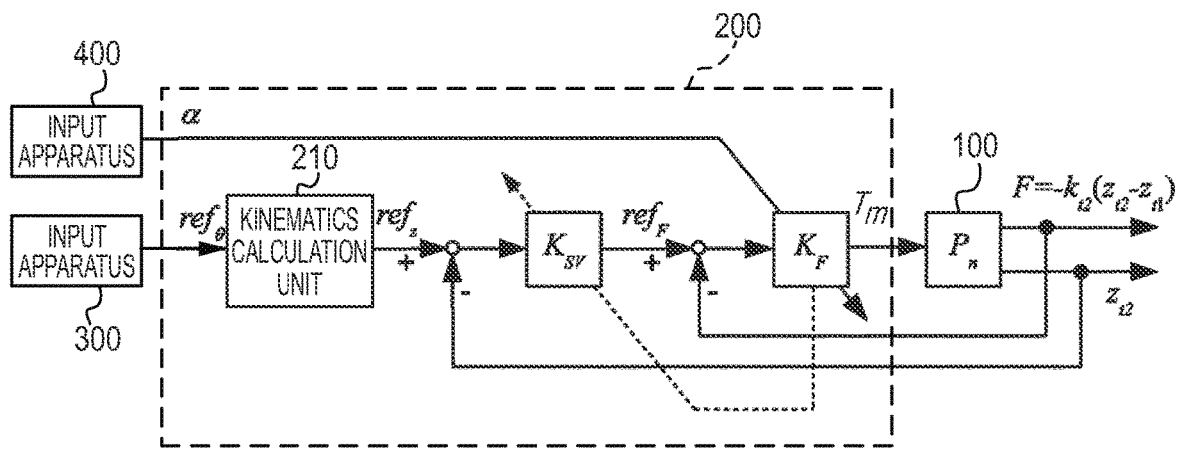
FIG. 20A shows an example of a schematic configuration of a control system for the continuum robot according to a fourth embodiment of the present disclosure.
Figure 20B:
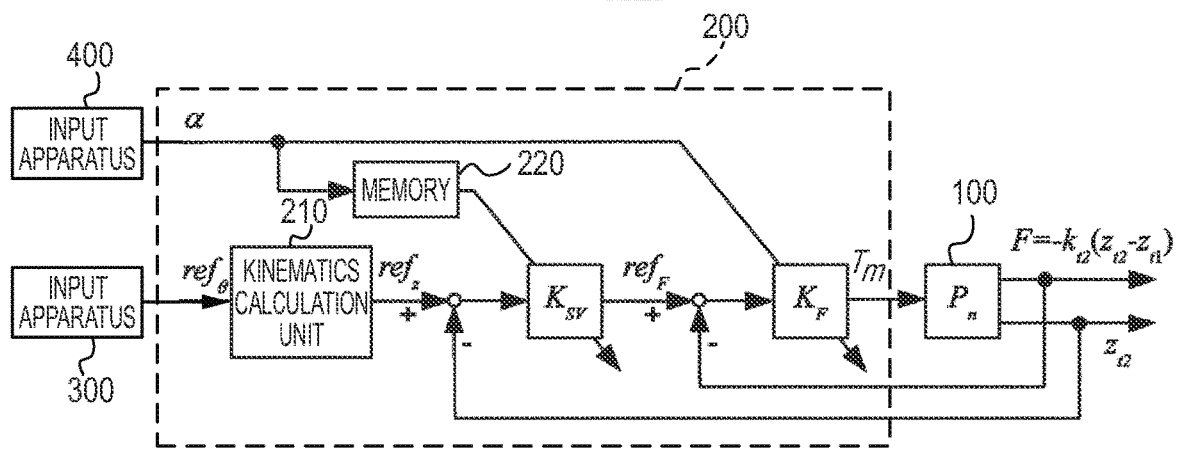
FIG. 20B shows an example of a schematic configuration of a control system for the continuum robot according to the fourth embodiment of the present disclosure.
Figure 20C:
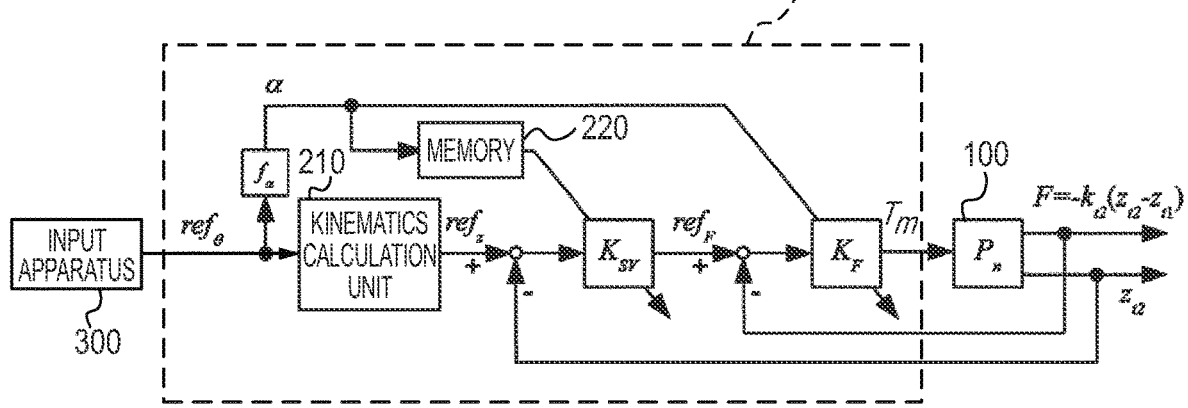
FIG. 20C shows an example of a schematic configuration of a control system for the continuum robot according to the fourth embodiment of the present disclosure.

FIGS. 20A to 20C show an example of a schematic configuration of the control system 10 for a continuum robot according to the fourth embodiment of the present disclosure. Hereinafter, the control system 10 of the continuum robot shown in FIG. 20A will be described as "a control system 10-2 of the continuum robot". The control system 10 of the continuum robot shown in FIG. 20B is described as "a control system 10-3 of the continuum robot". The control system 10 of the continuum robot shown in FIG. 20C is described as "a control system 10-4 of the continuum robot". In FIGS. 20A to 20C, components similar to those shown in FIG. 1 are denoted by the same reference numerals, and a detailed description thereof is omitted.

In the control system 10-2 of the continuum robot shown in FIG. 20A, the broken line indicates that the position control unit $K_{SV}$ is redesigned in accordance with the variation of the force control unit $K_F$. Specifically, FIG. 20A shows the first gain obtained by multiplying the gain of the force control unit $K_F$ by the coefficient (the first coefficient) $\alpha$. In FIG. 20A, the coefficient (the first coefficient) $\alpha$ is input from the input apparatus 400 to the force control unit $K_F$. Then, on the computer, the procedure of increasing the gain (a second gain) of the position control unit $K_{SV}$ in small steps and calculating the response of the open-loop transfer function $G_{cl}K_{SV}$ to confirm that the servo band is the same as when the coefficient $\alpha$ is 1 may be repeated and repeated. However, if the coefficient $\alpha$ is too small, the position control unit $K_{SV}$ must have a high gain, which excites the higher-order mode and causes the control system to become unstable. Therefore, the lower limit of the coefficient $\alpha$ may be set in advance. Alternatively, a coefficient (a second coefficient) to be multiplied by the gain of the position control unit $K_{SV}$ is previously calculated and stored in a memory so that the servo band of the position control unit $K_{SV}$ is always equal according to the coefficient $\alpha$. In this case, for example, as in the control system 10-3 of the continuum robot shown in FIG. 20B, the coefficient (the second coefficient) multiplied by the gain of the position control unit $K_{SV}$ may be read from the memory 220 in accordance with the coefficient $\alpha$. As a result, the back drivability can be changed in real time by adding a knob or the like to the operation system of the continuum robot 100 which allows the operator to arbitrarily command the coefficient $\alpha$.

Next, a control system for varying the back drivability in conjunction with the curving angle of the curvable unit 110 will be described. For example, in order to reduce back drivability as the curve becomes larger and prevent deformation due to disturbance or the like, the following equation (34) may be used.

$$\alpha = \beta |ref_\theta| \qquad (34)$$

On the other hand, in order to increase the back drivability and the safety as the curve becomes larger, the following equation (35) may be used.

$$\alpha = -\beta |ref_\theta| + \gamma \qquad (35)$$

Here, $\beta$ and $\gamma$ are coefficients, and the range of curvature must be set in advance so that the coefficient $\alpha$ falls within the range of $0<\alpha<1$. FIG. 20C shows a block diagram thereof. Here, the coefficient calculating section fa represents a means for calculating and changing the coefficient (the first coefficient) $\alpha$ in accordance with the target curving angle ref$\theta$ of the curvable unit 110, as shown in equations (34) and (35).

Figure 21:
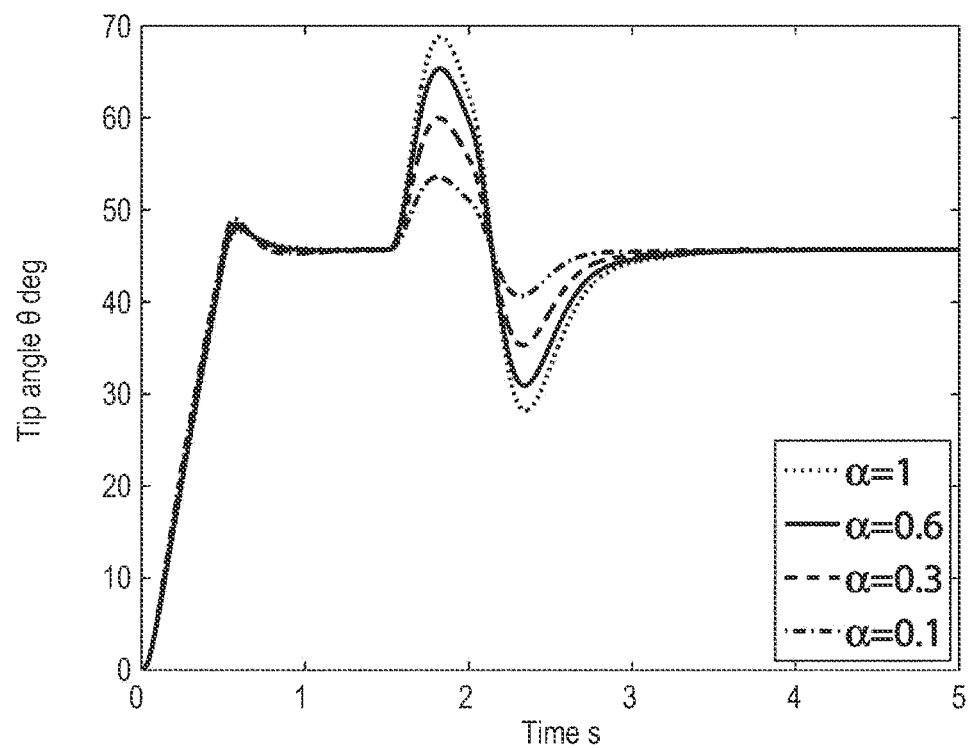
FIG. 21 is a diagram showing a simulation response by a control system according to a control system of the continuum robot according to the fourth embodiment of the present disclosure.

FIG. 21 is a diagram showing a simulation response by the control system according to the control system 10 of the continuum robot according to the fourth embodiment of the present disclosure. In the same manner as in the first embodiment, a disturbance torque shown in FIG. 12F, for example, is applied to the tip of the curvable unit 110 1.5 seconds after the positioning is completed. In FIG. 21, the curving angle of the tip of the curvable unit 110 is shown, and responses with coefficients $\alpha$ of 1, 0.6, 0.3, and 0.1 are indicated by dotted lines, solid lines, dashed lines, and dashed dotted lines, respectively. Although the positioning performance does not change with the change of the coefficient $\alpha$, it can be seen that the back drivability decreases as the coefficient $\alpha$ decreases. As a result, it can be seen that a control system capable of adjusting the magnitude of the back drivability can be realized without changing the positioning performance.

Fifth Embodiment

Next, a fifth embodiment of the present disclosure will be described. In the description of the fifth embodiment described below, matters common to the above-described first to fourth embodiments will be omitted, and matters different from the above-described first to fourth embodiments will be described.

In the first to fourth embodiments described above, the observed values are the displacement $z_{t1}$ and $z_{t2}$ on the base of the wire holding mechanism and the tip side. However, a displacement sensor capable of realizing the displacement sensor may not be arranged due to the limitation of the mechanism. Therefore, in the present embodiment, a control system using other observed quantities will be described.

If the displacement $z_{t2}$ of the wire holding mechanism is difficult to observe and the spring displacement $k_{t2}$ of the tension detection mechanism can be observed by a strain gauge or the like, the generated force F may be taken as an observed quantity. In this case, the displacement $z_{t2}$ of the wire holding mechanism is determined by the following equation (36).

$$z_{t2} = z_{t1} - F/k_{t2} \qquad (36)$$

When the spring displacement of the force detection unit is sufficiently small in practical use compared with the moving range of the wire holding mechanism, the control amount of the outer loop control system (a second loop control system) may be set as the displacement $z_{t1}$ of the wire holding mechanism base unit.

Further, if it is difficult to observe the displacement $z_{t1}$ of the wire holding mechanism base unit, and the spring coefficient of the coupling and the spring coefficient $k_g$, $k_{t1}$ of the drive shaft in the z-direction are sufficiently large, the rotation angle $\theta_m$ of the motor may be observed, approximated by the following equation (37), and used as the position control quantity of the outer loop control system (the second loop control system).

$$z_{t1} \cong p \cdot \theta_m \tag{37}$$

Sixth Embodiment

Next, a sixth embodiment of the present disclosure will be described. In the description of the sixth embodiment described below, matters common to the first to fifth embodiments described above will be omitted, and matters different from the first to fifth embodiments described above will be described.

In the above-described first to fifth embodiments, control system design was performed for the continuum robot 100 driven in the plane. In the present embodiment, a control system design is performed for a continuum robot capable of three-dimensional driving.

Figure 22:
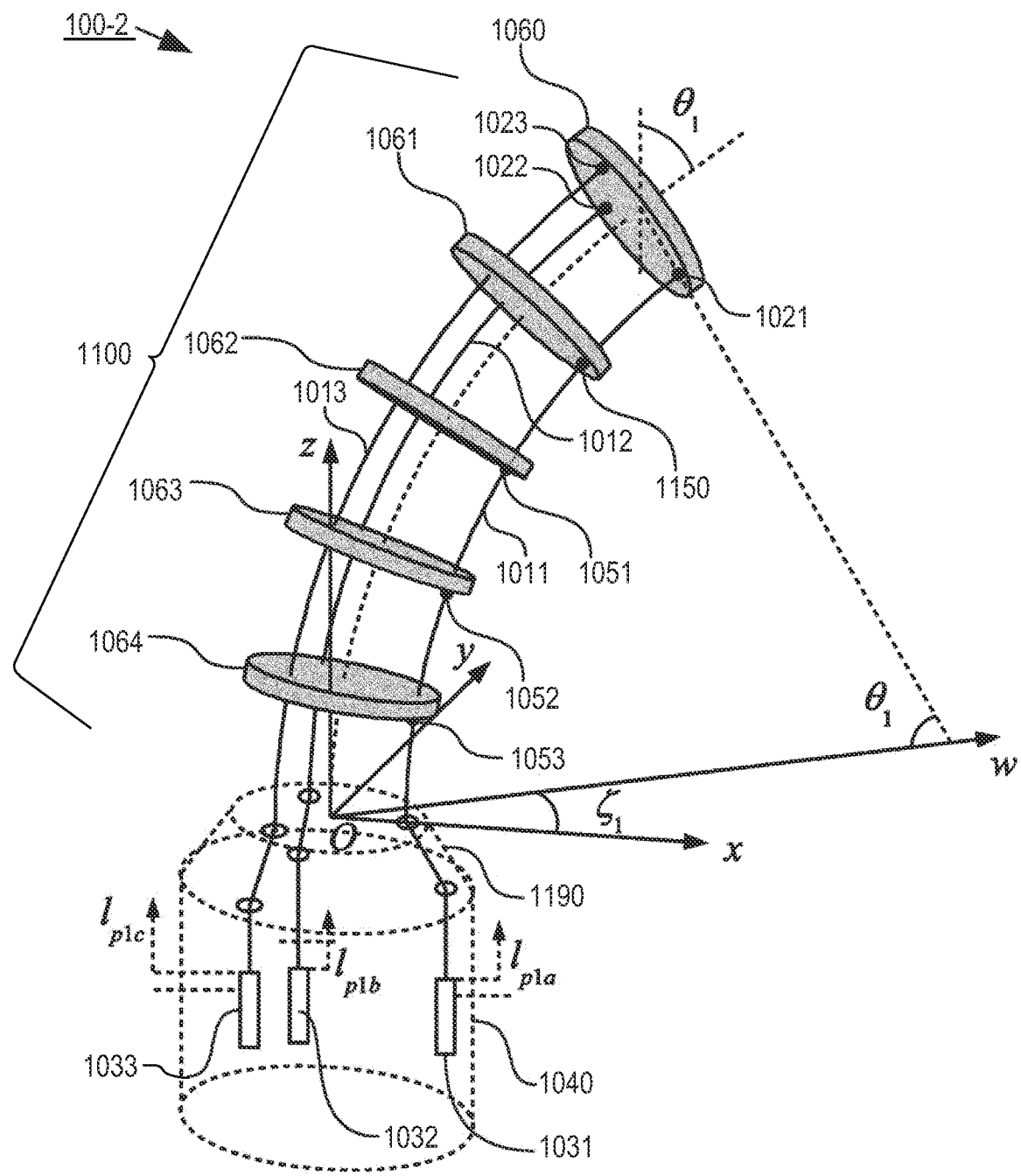
FIG. 22 is a diagram showing a first example of a schematic configuration of the continuum robot according to a sixth embodiment of the present disclosure.

FIG. 22 is a diagram showing a first example of a schematic configuration of a continuum robot 100 according to the sixth embodiment of the present disclosure. Hereinafter, the continuum robot 100 shown in FIG. 22 will be described as "a continuum robot 100-2".

In the continuum robot 100-2 shown in FIG. 22, wires 1011 to 1013 are connected to fixed portions 1021 to 1023 at a distal end 1060 of the curvable unit 1100. Wire holding pipes 1031 to 1033 are connected to the proximal end of the wires 1011 to 1013. Similar to the first embodiment, a robot base unit 1040 is provided with wire holding mechanisms (not shown in FIG. 22) and actuators (not shown in FIG. 22) for each wire in the wires 1011 to 1013. The wire holding mechanism is connected to the actuator via a wire holding mechanism base unit (not shown in FIG. 22), and is movable up and down. The wire holding pipes 1031 to 1033 are connected to wire holding mechanisms, and these attitudes are controlled by pushing and pulling with actuators. The continuum robot 100-2 has wire guides 1061 to 1064 which are members for guiding the wires 1011 to 1013. The wire guide may be a continuum member such as a bellows member or a mesh member in addition to a method of discretely arranging a plurality of members. The wire guides 1061 to 1064 are fixed to the wire 1011 at a fixing units 1050 to 1053. Further, the distance between the wires 1011 to 1013 and the wire holding pipes 1031 to 1033 may be different. In this case, the diameter converting unit 1190 may be connected to the robot base unit 1040. In FIG. 22, the central axis of the continuum robot 100-2 is indicated by a broken line.

In the present embodiment, the mechanism comprising the wires 1011 to 1013 and the wire guides 1061 to 1064 are referred to as a curvable unit 1100 which is a continuum portion. The actuator unit comprising a rotary motor and a rotational linear motion conversion mechanism is used for the actuator (not shown). Further, the wire holding mechanism has a function of detecting the tension of the wire. For this purpose, the above-described wire holding mechanism base unit is provided between the wire holding mechanism and the actuator, the wire holding mechanism base unit is connected to the actuator, and the wire holding mechanism base unit and the wire holding mechanism are connected by a spring. At this time, it is preferable to provide a linear guide so that the wire holding mechanism is displaced only in the z-axis direction or to use a parallel spring for the spring. The tension of the wire can be detected by measuring the displacement of the spring. The definitions of the symbols shown in FIG. 22 are described below.

$l_d$: Length of the central axis of the curvable unit 1100.
$\theta_n$: Curving angle of the distal end of the curvable unit 1100.
$\zeta_n$: Turning angle of the distal end of the curvable unit 1100.
$\rho_n$: Radius of curvature of the curvable unit 1100.

In the present embodiment, the wires 1011 to 1013 are referred to as wire "a", wire "b", and wire "c" in a counterclockwise direction in the xy plane, and the driving displacements of the wires "a" to "c" 1011 to 1013 are referred to as "$l_{pla}$", "$l_{plb}$", and "$l_{plc}$".

Figure 23:
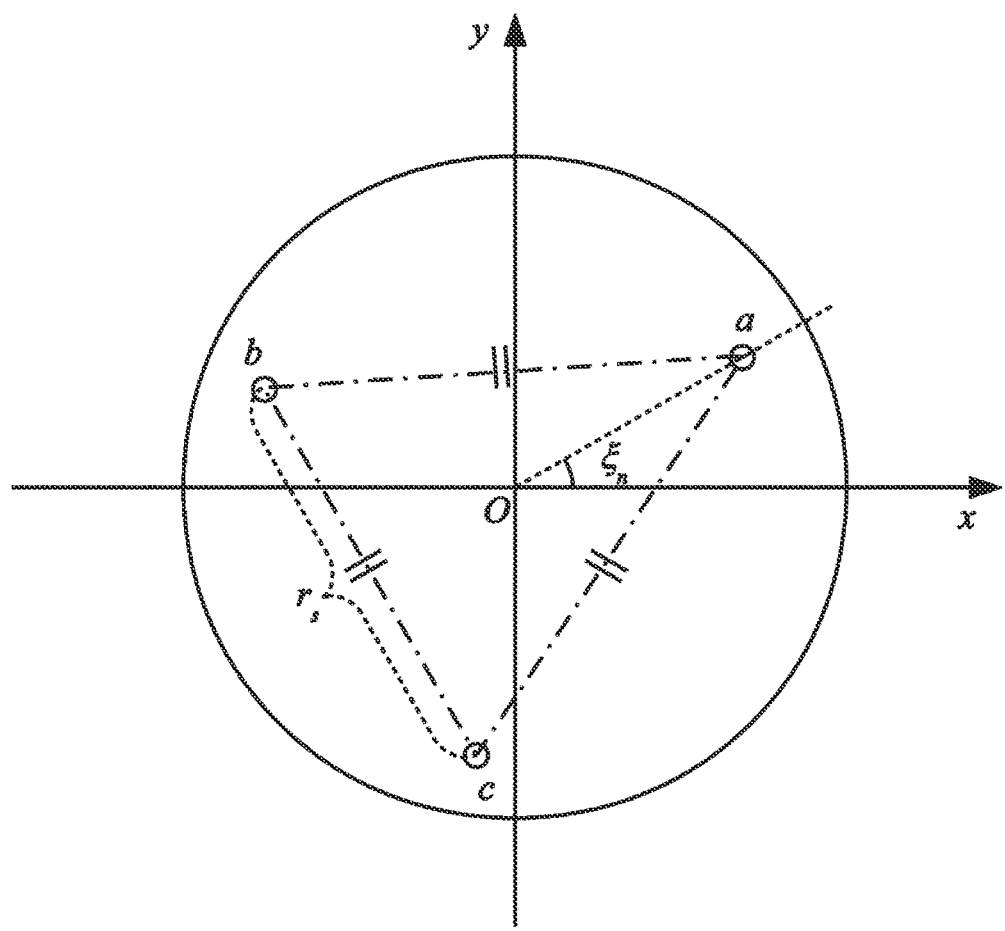
FIG. 23 shows an example of a wire arrangement of the continuum robot according to the sixth embodiment of the present disclosure.

FIG. 23 is a diagram showing an example of the arrangement of wires of the continuum robot 100 according to the sixth embodiment of the present disclosure. As shown in FIG. 23, the wires "a" to "c" 1011 to 1013 are arranged at the apexes of an equilateral triangle whose length is $r_s$, and the phase angle $\xi_n$ is an angle for determining the arrangement of the wires. In the present embodiment, $\xi_1=0$.

In the present embodiment, the kinematics of the continuum robot 100-2 is derived by making the following assumptions.

[1] In each curvable unit 110, the wire is deformed to constant curvature.
[2] Torsional deformation of the wire is not taken into account.
[3] The wire is not deformed in the longitudinal direction.
[4] Friction between the wire guide and the wire is not taken into account.

As a result, the driving displacement $l_{pla}$ of the wire "a", the driving displacement $l_{plb}$ of the wire "b", and the driving displacement $l_{plc}$ of the wire "c" for setting the curving angle $\theta_1$ and the turning angle $\zeta_1$ of the distal end of the curvable unit 110 are expressed by the following equation (38).

$$l_{pla} = -\frac{r_s}{\sqrt{3}}\cos(\zeta_1 - \xi_1)\theta_1 \tag{38}$$

$$l_{plb} = -\frac{r_s}{\sqrt{3}}\cos\left(\frac{2\pi}{3} - \zeta_1 + \xi_1\right)\theta_1$$

$$l_{plc} = -\frac{r_s}{\sqrt{3}}\cos\left(\frac{4\pi}{3} - \zeta_1 + \xi_1\right)\theta_1$$

In the present embodiment, distributed control applying the double-loop control of the first to fifth embodiments is performed independently for each wire in the wires "a" to "c" 1011 to 1013.

Figure 24:
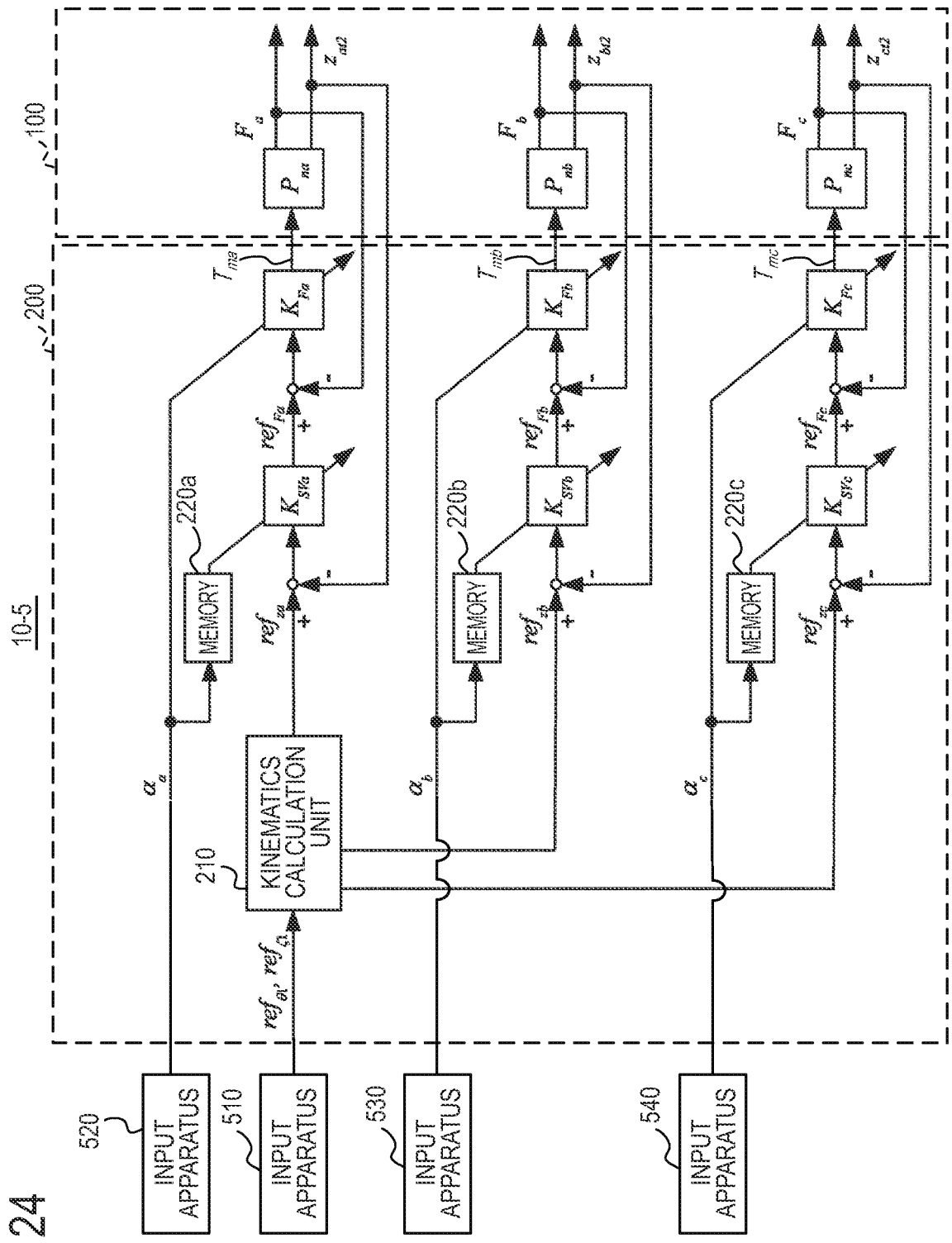
FIG. 24 shows an example of a schematic configuration of a control system for the continuum robot including the continuum robot shown in FIG. 22 according to the sixth embodiment of the present disclosure.

FIG. 24 is a diagram showing an example of a schematic configuration of the control system 10 for the continuum robot including the continuum robot 100-2 shown in FIG. 22 according to a sixth embodiment of the present disclosure. Hereinafter, the control system 10 of the continuum robot shown in FIG. 24 will be described as "a control system 10-5 of the continuum robot". In FIG. 24, components similar to those shown in FIG. 1 are denoted by the same reference numerals, and a detailed description thereof will be omitted.

In FIG. 24, a target curving angle ref$\theta_1$ and a target turning angle ref$\zeta_1$ at the distal end of the curvable unit 110 are input from the input apparatus 510 to the kinematics calculation unit 210. The target displacements ref$_{za}$, ref$_{zb}$, and ref$_{zc}$ of each wire holding mechanism are obtained by substituting the target curving angle ref$\theta_1$ and the target turning angle ref$\zeta_1$ into the curving angle $\theta_1$ and the turning angle Li of the equation (38), respectively. The dynamic model P$_{na}$ is equivalent to the dynamic model P$_n$ of the first embodiment in that the wire "a" is driven by fixing the wire holding pipes of the wire "b" and the wire "c" to the actuator base unit. Similarly, the dynamic model P$_{nb}$ is equivalent to the dynamic model P$_n$ of the first embodiment in that the wire holding pipes of the wires "a" and "c" are fixed to the actuator base unit and the wire "b" is driven. Similarly, the dynamic model P$_{nc}$ is obtained as equivalent to the dynamic model P$_n$ of the first embodiment by fixing the wire holding pipes of the wires "a" and "b" to the actuator base unit and driving the wire "c". K$_{Fa}$, K$_{Fb}$, and K$_{Fc}$ are force control units for the wires "a", "b", and "c". The force control units may be individually designed or may be the same control system, especially if there is no difference in the dynamic models P$_{na}$, P$_{nb}$, and P$_{nc}$. K$_{SVa}$, K$_{SVb}$, and K$_{SVc}$ are position control units for the wires "a", "b", and "c". The position control units may be individually designed, or may be the same control system, especially if there is no difference in the dynamic models P$_{na}$, P$_{nb}$, and P$_{nc}$.

The coefficients da, ab, and ac are coefficients for varying the back drivability shown in the fourth embodiment. Specifically, in FIG. 24, the coefficient da is input from the input apparatus 520 to the force control unit K$_{Fa}$ or the like, the coefficient ab is input from the input apparatus 530 to the force control unit K$_{Fb}$ or the like, and the coefficient de is input from the input apparatus 540 to the force control unit K$_{Fc}$ or the like. In this case, if the coefficients da, ab, and ac are set to different values, the back drivability can be varied in accordance with the turning direction. If the coefficients $\alpha_a$, $\alpha_b$, and $\alpha_c$ are all set to the same value, uniform back drivability can be obtained regardless of the turning direction.

If the back drivability of one of the 3 wires is greatly reduced, only the back drivability with respect to the disturbance in the central axis direction of the continuum robot 100-2 can be reduced, and the disturbance torque in the curving direction can be provided with the back drivability. This can prevent the curvable unit 1100 from colliding with the base unit and, conversely, can prevent the curvable unit 1100 from being extended in the positive z-axis direction and causing the wire holding mechanism to collide with the base unit.

Further, in order to set the back drivability to the disturbance in the center axis direction of the continuum robot 100-2 to 0 and to provide the back drivability to the disturbance in the curving direction, one wire or the wire holding pipe may be fixed to the actuator base unit.

Figure 25:
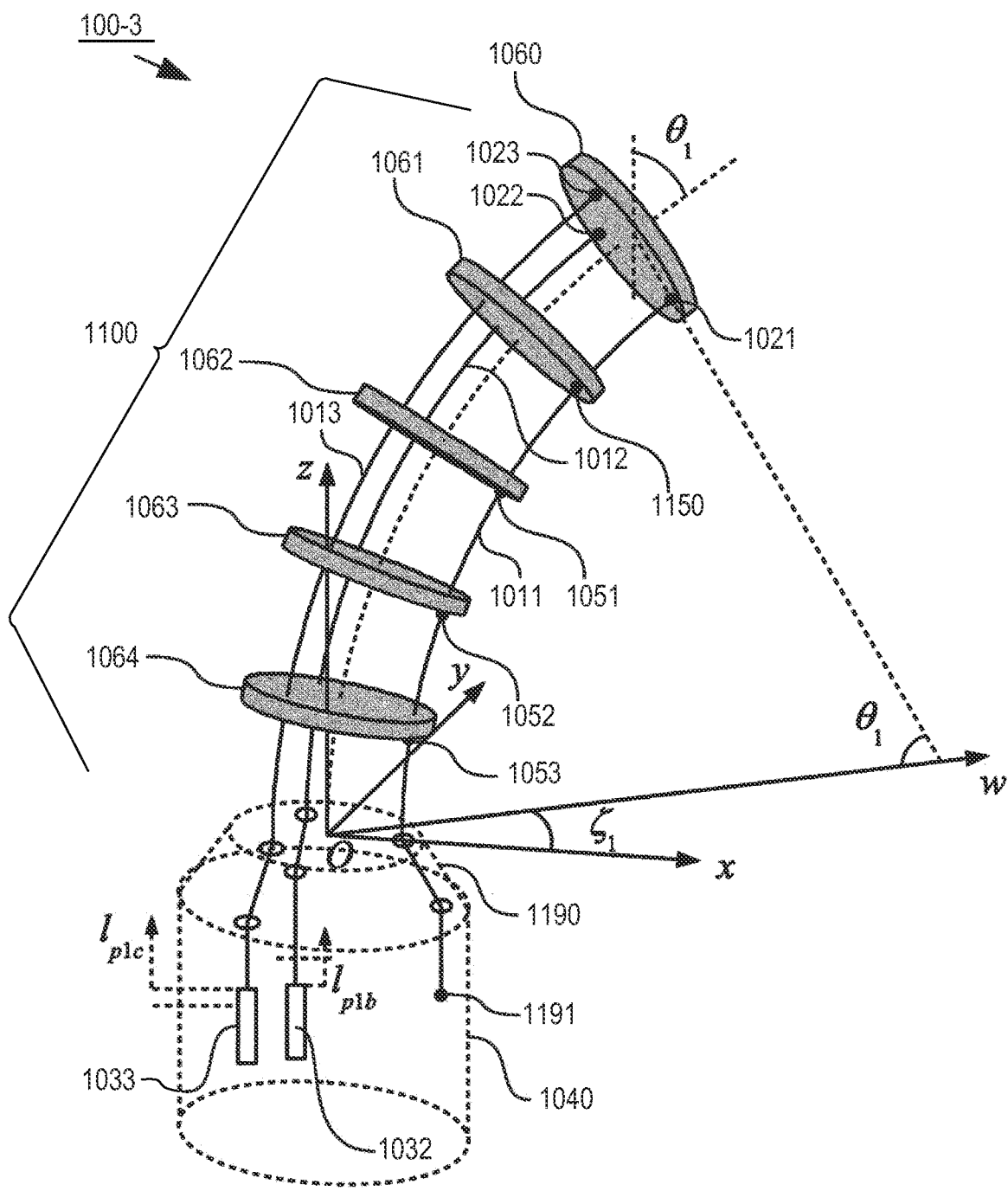
FIG. 25 is a diagram showing a second example of a schematic configuration of the continuum robot according to the sixth embodiment of the present disclosure.

FIG. 25 is a diagram showing a second example of a schematic configuration of the continuum robot 100 according to the sixth embodiment of the present disclosure. Hereinafter, the continuum robot 100 shown in FIG. 25 will be described as "a continuum robot 100-3". In FIG. 25, components similar to those shown in FIG. 22 are denoted by the same reference numerals. Specifically, FIG. 25 shows an example of fixing the wire "a" 1011 to the fixing unit 1191. At this time, the driving displacement $l_{p1b}$ of the wire "b" and the driving displacement $l_{p1c}$ of the wire "c" for setting the curving angle $\theta_1$ and the turning angle $\zeta_1$ of the distal end of the curvable unit 1100 are expressed by the following equations (39) and (40), respectively.

$$l_{p1b} = r_s \cos\left(\frac{\pi}{6} + \zeta_1\right)\theta_1 \quad (39)$$

$$l_{p1c} = r_s \cos\left(\frac{\pi}{6} - \zeta_1\right)\theta_1 \quad (40)$$

Figure 26:
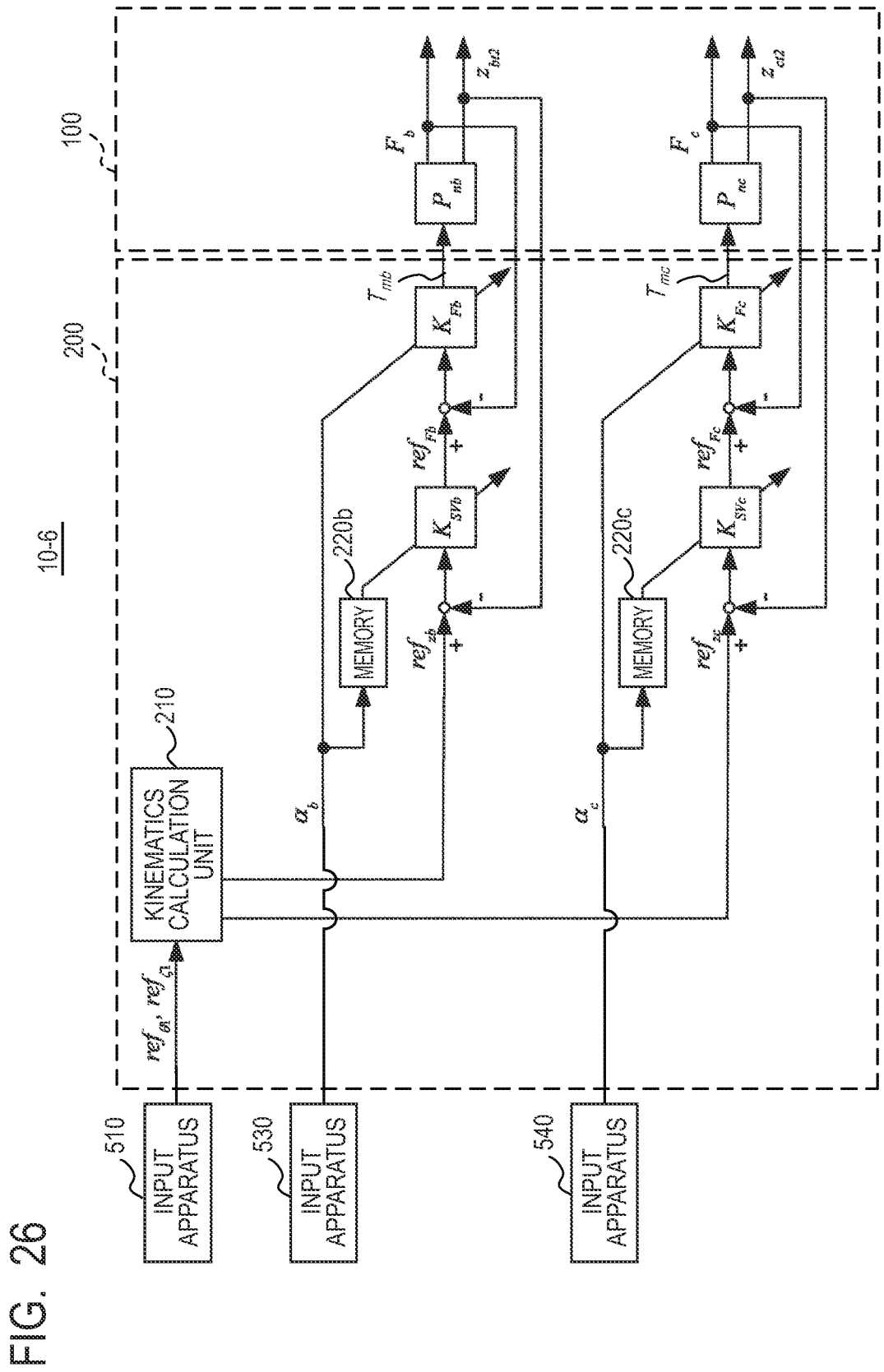
FIG. 26 shows an example of a schematic configuration of a control system for the continuum robot including the continuum robot shown in FIG. 25 according to the sixth embodiment of the present disclosure.

FIG. 26 is a diagram showing an example of a schematic configuration of the control system 10 for a continuum robot including the continuum robot 100-3 shown in FIG. 25 according to the sixth embodiment of the present disclosure. In FIG. 26, the target displacements ref$_{zb}$ and ref$_{zc}$ of each wire holding mechanism are obtained by substituting the target curving angle ref$\theta_1$ and the target turning angle ref$\zeta_1$ into the curving angle $\theta_1$ and turning angle $\zeta_1$ of the equations (39) and (40).

Seventh Embodiment

Next, a seventh embodiment of the present disclosure will be described. In the description of the seventh embodiment described below, matters common to the first to sixth embodiments described above will be omitted, and matters different from the first to sixth embodiments described above will be described.

In the first to sixth embodiments described above, the control for improving the back drivability of the continuum robot 100 having a single curvable unit has been described. In the present embodiment, a control system design method for the continuum robot having a plurality of curvable units will be described.

Figure 27:
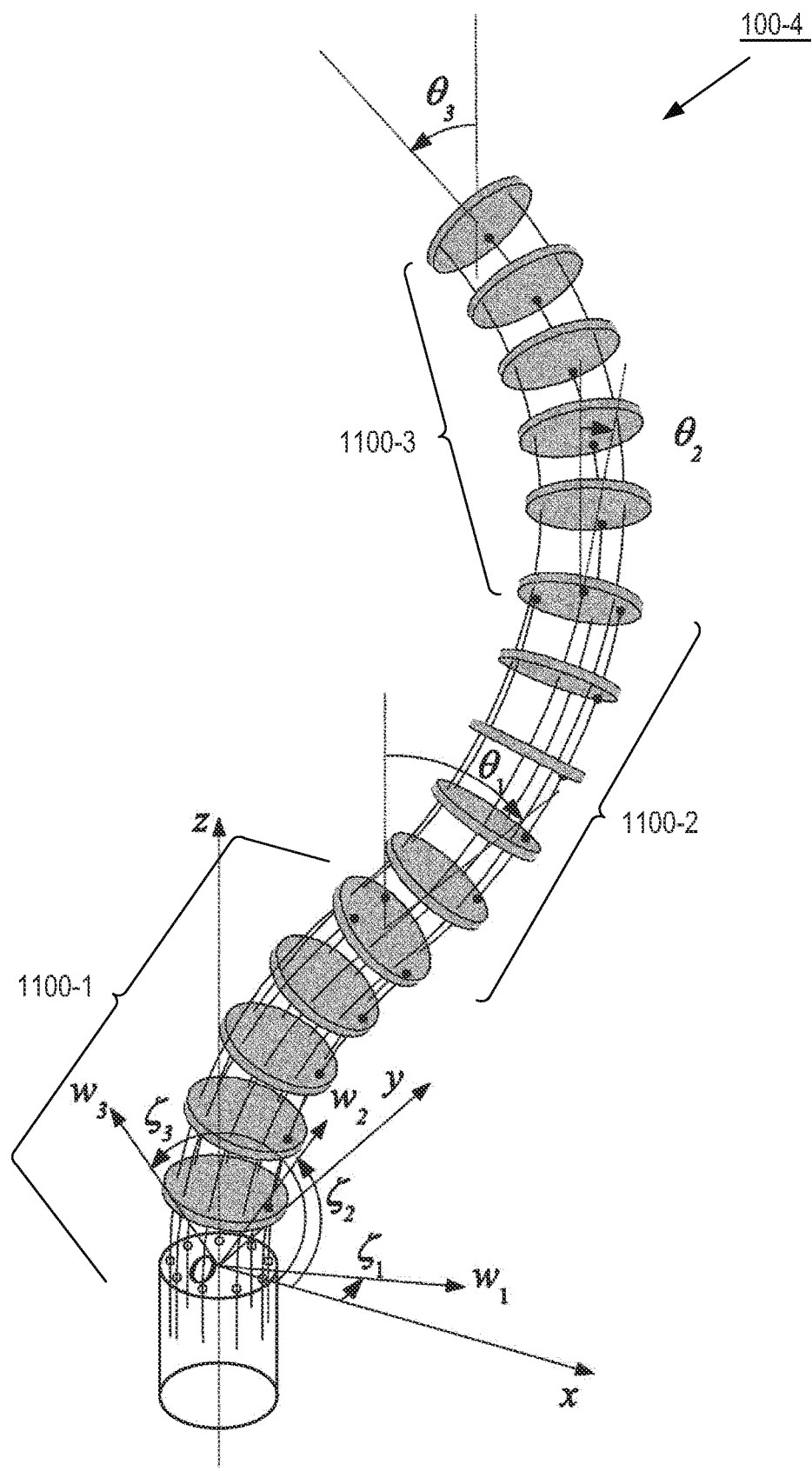
FIG. 27 shows a second example of a schematic configuration of the continuum robot 100 according to a seventh embodiment of the present disclosure.

FIG. 27 is a diagram showing a second example of a schematic configuration of the continuum robot 100 according to the seventh embodiment of the present disclosure. Hereinafter, the continuum robot 100 shown in FIG. 27 will be described as "a continuum robot 100-4". In FIG. 27, three curvable units 1100-1 to 1100-3 are shown.

Here, the driving displacements of the wires driving the n-th curvable unit are set to $l_{pna}$, $l_{pnb}$, and $l_{pnc}$, and the relationship between the driving displacements $l_{pna}$, $l_{pnb}$, and $l_{pnc}$ of the wires "a", "b", and "c" of the continuum robot 100-4 having a plurality of curvable units 1100, and the curving angle $\theta_n$ and the turning angle $\zeta_n$ of the distal end of the n-th curvable unit is determined. The number of curvable units is denoted by "e", and the phase angle of the wire driving the n-th curvable unit is expressed by the following equation (41).

$$\xi_n = \frac{120}{e}n \quad (41)$$

As a result, the driving displacements $l_{pna}$, $l_{pnb}$, and $l_{pnc}$ of the wire of the n-th curvable unit are expressed by the following equation (42).

$$l_{pna} = -\frac{r_s}{\sqrt{3}}\cos(\zeta_n - \xi_n)\theta_n \quad (42)$$

$$l_{pnb} = -\frac{r_s}{\sqrt{3}}\cos\left(\frac{2\pi}{3} - \zeta_n + \xi_n\right)\theta_n$$

$$l_{pnc} = -\frac{r_s}{\sqrt{3}}\cos\left(\frac{4\pi}{3} - \zeta_n + \xi_n\right)\theta_n$$

As in the sixth embodiment, each wire is driven by a double-loop control system. Further, in order to prevent collision due to back drive between the curvable units, as in the sixth embodiment, for example, the wire "a" of each curvable unit is fixed and the back drivability in the central axis direction of the continuum robot 100-4 is set to 0. At this time, the driving displacement $l_{pnb}$ of the wire "b" and the driving displacement $l_{pnc}$ of the wire "c" are expressed by the following expressions (43) and (44), respectively.

$$l_{pnb} = r_s \cos\left(\frac{\pi}{6} + \zeta_n\right)\theta_n \tag{43}$$

$$l_{pnc} = r_s \cos\left(\frac{\pi}{6} - \zeta_n\right)\theta_n \tag{44}$$

In the seventh embodiment, as in the sixth embodiment described above, back drivability is obtained only in the curving direction by driving the wire "b" and the wire "c" of each of the curvable units 1100 by the double-loop control system.

OTHER EMBODIMENTS

The present disclosure may also be implemented by providing a program that implements one or more of the functions of the above-described embodiments to a system or device via a network or storage medium, with one or more processors in the computer of the system or device reading and executing the program. It can also be realized by a circuit (for example, ASIC) which realizes one or more functions. This program and a computer readable storage medium storing the program are included in the present disclosure. As another embodiment of the present disclosure, a configuration in which the functional components of the control apparatus 200 of the continuum robot are incorporated into the continuum robot 100 is also applicable to the present disclosure.

It should be noted that the embodiments of the present disclosure described above are merely examples of embodiments for carrying out the present disclosure, and the technical scope of the present disclosure should not be construed in a limited manner. That is, the present disclosure can be practiced in various ways without departing from its technical philosophy or key features.

The present disclosure is not limited to the above embodiments, and various modifications and modifications are possible without departing from the spirit and scope of the disclosure. Accordingly, in order to make the scope of the present disclosure public, the following claims are attached.

According to the present disclosure, it is possible to realize high positioning performance of the curvable unit to the target position without complicated operation by the operator.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. A control system for controlling a continuum robot including at least a curvable unit driven by a wire and configured to be curvable and a driving unit driving the wire, comprising:
a position control unit configured to output a target tension of the wire, wherein the position control unit performs control so that an error between a target displacement for a push-pull driving of the wire by the driving unit and a displacement of a wire holding mechanism holding the wire obtained from the continuum robot is compensated; and
a force control unit configured to perform control so that an error between the target tension of the wire output from the position control unit and tension of the wire obtained from the continuum robot is compensated,
wherein a first loop control system including the force control unit, and a second loop control system including the force control unit and the position control unit are constituted,
wherein a first gain is calculated by multiplying a gain of the force control unit by a first coefficient and a second gain is calculated by multiplying a gain of the position control unit by a second coefficient, and
wherein the second gain is calculated according to the first gain.

2. The control system according to claim 1, further comprising a kinematics calculation unit calculating a kinematics calculation based on input of a target curving angle of the curvable unit to output the target displacement.

3. The control system according to claim 1,
wherein the first coefficient is varied according to the target curving angle of the curvable unit.

4. The control system according to claim 1,
wherein the continuum robot includes a plurality of the wires on one of the curvable unit and a plurality of the driving units driving each of the plurality of the wires, and
wherein the first loop control system and the second loop control system are configured to correspond to each driving unit in the plurality of the driving units.

5. The control system according to claim 4,
wherein one of the plurality of the wires in the one of the curvable unit is fixed to a base unit on the continuum robot.

6. A continuum robot comprising:
a wire;
at least a curvable unit configured to be curvable; and
a driving unit driving the wire,
wherein the continuum robot includes a control system according to claim 1.

7. A control system for controlling a continuum robot including at least a curvable unit driven by a wire and configured to be curvable and a driving unit driving the wire, comprising:
a position control unit configured to output a target tension of the wire, wherein the position control unit performs control so that an error between a target displacement for a push-pull driving of the wire by the driving unit and a displacement of a wire holding mechanism holding the wire obtained from the continuum robot is compensated; and
a force control unit configured to perform control so that an error between the target tension of the wire output from the position control unit and tension of the wire obtained from the continuum robot is compensated,
wherein a first loop control system including the force control unit, and a second loop control system including the force control unit and the position control unit are constituted, and
wherein the force control unit repeats a process of calculating a transfer function based on a motion equation of the continuum robot and an open-loop transfer function of the force control unit, and a process of calculating a stability margin from the open-loop transfer function to determine a gain of the force control unit.

8. A continuum robot comprising:
a wire;
at least a curvable unit configured to be curvable; and
a driving unit driving the wire,
wherein the continuum robot includes a control system according to claim 7.

9. A control system for controlling a continuum robot including at least a curvable unit driven by a wire and configured to be curvable and a driving unit driving the wire, comprising:
a position control unit configured to output a target tension of the wire, wherein the position control unit performs control so that an error between a target displacement for a push-pull driving of the wire by the driving unit and a displacement of a wire holding mechanism holding the wire obtained from the continuum robot is compensated; and
a force control unit configured to perform control so that an error between the target tension of the wire output from the position control unit and tension of the wire obtained from the continuum robot is compensated,
wherein a first loop control system including the force control unit, and a second loop control system including the force control unit and the position control unit are constituted,
wherein the force control unit includes a PID controller and a low-pass filter coupled in series, and
wherein a differential gain of the PID controller is determined by repeating a process of setting the differential gain and a process of calculating the open-loop transfer function using the transfer function based on the motion equation of the force control unit and the continuum robot.

10. A continuum robot comprising:
a wire;
at least a curvable unit configured to be curvable; and
a driving unit driving the wire,
wherein the continuum robot includes a control system according to claim 9.

11. A control system for controlling a continuum robot including at least a curvable unit driven by a wire and configured to be curvable and a driving unit driving the wire, comprising:
a position control unit configured to output a target tension of the wire, wherein the position control unit performs control so that an error between a target displacement for a push-pull driving of the wire by the driving unit and a displacement of a wire holding mechanism holding the wire obtained from the continuum robot is compensated; and
a force control unit configured to perform control so that an error between the target tension of the wire output from the position control unit and tension of the wire obtained from the continuum robot is compensated,
wherein a first loop control system including the force control unit, and a second loop control system including the force control unit and the position control unit are constituted, and
wherein the force control unit includes a PID controller, a phase lead filter, and a low-pass filter coupled in series.

12. The control system according to claim 11,
wherein the phase lead filter is determined by repeating a process of setting a break frequency and a process of calculating the open-loop transfer function using the transfer function based on the motion equation of the force control unit and the continuum robot.

13. A continuum robot comprising:
a wire;
at least a curvable unit configured to be curvable; and
a driving unit driving the wire,
wherein the continuum robot includes a control system according to claim 11.

* * * * *